(12) United States Patent
Wenger et al.

(10) Patent No.: US 9,314,566 B2
(45) Date of Patent: Apr. 19, 2016

(54) PORTABLE INFUSION PUMP AND MEDIA PLAYER

(75) Inventors: Mitchell Wenger, Ross, CA (US); Mark C. Estes, Malibu, CA (US); Scott Chiang, San Jose, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 556 days.

(21) Appl. No.: 13/613,375

(22) Filed: Sep. 13, 2012

(65) Prior Publication Data
US 2013/0060225 A1     Mar. 7, 2013

Related U.S. Application Data

(60) Continuation of application No. 12/968,741, filed on Dec. 15, 2010, now Pat. No. 8,282,626, which is a division of application No. 11/954,755, filed on Dec. 12, 2007, now Pat. No. 7,875,022.

(51) Int. Cl.
*A61M 5/172* (2006.01)
*A61M 5/142* (2006.01)
(Continued)

(52) U.S. Cl.
CPC ......... *A61M 5/14244* (2013.01); *A61M 5/1413* (2013.01); *A61M 5/1452* (2013.01); *A61M 5/14566* (2013.01); *A61M 2005/14268* (2013.01); *A61M 2005/31518* (2013.01); *A61M 2205/18* (2013.01); *A61M 2205/3561* (2013.01); *A61M 2205/3569* (2013.01); *A61M 2205/3584* (2013.01); *A61M 2205/3592* (2013.01); *A61M 2205/502* (2013.01); *A61M 2205/581* (2013.01); *A61M 2205/582* (2013.01);
(Continued)

(58) Field of Classification Search
CPC ................. A61M 5/14244; A61M 2205/3592; A61M 2205/18; A61M 2205/3584; A61M 2205/502; G06F 1/163
USPC ........................... 604/66, 67, 503, 27; 700/94
See application file for complete search history.

(56) References Cited

U.S. PATENT DOCUMENTS 4,768,506 A * 9/1988 Parker et al. ................... 606/174
5,029,591 A * 7/1991 Teves ............................ 600/528
(Continued)

FOREIGN PATENT DOCUMENTS

WO    WO 2004/041330    5/2004
WO    WO 2004/056412    7/2004
(Continued)

OTHER PUBLICATIONS

Accu-Chek Spirit, "Pump Therapy Made for You," Roche, 2006, 6 pages.
(Continued)

*Primary Examiner* — Nathan R Price
*Assistant Examiner* — William Carpenter
(74) *Attorney, Agent, or Firm* — Fish & Richardson P.C.

(57) ABSTRACT

Some embodiments of a portable infusion pump system can be configured to deliver medicine (e.g., insulin or the like) to a user and to deliver media content to a user. The media content can include, for example, MP3 music and other audio/video data stored in a memory device in the portable system. Thus, in particular embodiments, the portable infusion pump system can serve a dual purpose of providing medication and entertainment for the user from a compact and unobtrusive device.

16 Claims, 20 Drawing Sheets

(51) Int. Cl.
G06F 1/16 (2006.01)
A61M 5/14 (2006.01)
A61M 5/145 (2006.01)
A61M 5/315 (2006.01)

(52) U.S. Cl.
CPC ..... *A61M 2205/583* (2013.01); *A61M 2205/80* (2013.01); *A61M 2209/01* (2013.01); *G06F 1/163* (2013.01)

(56) References Cited

U.S. PATENT DOCUMENTS

| | | | |
|---|---|---|---|
| 5,349,575 A | 9/1994 | Park | |
| 5,914,941 A * | 6/1999 | Janky | H04L 69/04 370/313 |
| 6,248,067 B1 | 6/2001 | Causey, III et al. | |
| 6,251,113 B1 * | 6/2001 | Appelbaum et al. | 606/107 |
| 6,269,340 B1 | 7/2001 | Ford et al. | |
| 6,292,440 B1 * | 9/2001 | Lee | G11B 19/04 369/7 |
| 6,485,461 B1 | 11/2002 | Mason et al. | |
| 6,551,276 B1 | 4/2003 | Mann et al. | |
| 6,554,798 B1 | 4/2003 | Mann et al. | |
| 6,558,320 B1 | 5/2003 | Causey, III et al. | |
| 6,641,533 B2 | 11/2003 | Causey, III et al. | |
| 6,656,158 B2 | 12/2003 | Mahoney et al. | |
| 6,656,159 B2 | 12/2003 | Flaherty et al. | |
| 6,659,978 B1 | 12/2003 | Kasuga et al. | |
| 6,669,669 B2 | 12/2003 | Flaherty et al. | |
| 6,692,457 B2 | 2/2004 | Flaherty | |
| 6,699,218 B2 | 3/2004 | Flaherty et al. | |
| 6,723,072 B2 | 4/2004 | Flaherty et al. | |
| 6,740,059 B2 | 5/2004 | Flaherty et al. | |
| 6,744,350 B2 * | 6/2004 | Blomquist | A61M 5/142 340/309.16 |
| 6,749,587 B2 | 6/2004 | Flaherty | |
| 6,768,425 B2 | 7/2004 | Flaherty et al. | |
| 6,809,653 B1 | 10/2004 | Mann et al. | |
| 6,830,558 B2 | 12/2004 | Flaherty et al. | |
| 6,872,200 B2 | 3/2005 | Mann et al. | |
| 6,936,029 B2 | 8/2005 | Mann et al. | |
| 6,960,192 B1 | 11/2005 | Flaherty et al. | |
| 6,979,326 B2 | 12/2005 | Mann et al. | |
| 6,997,920 B2 | 2/2006 | Mann et al. | |
| 7,018,360 B2 | 3/2006 | Flaherty et al. | |
| 7,025,743 B2 | 4/2006 | Mann et al. | |
| 7,029,455 B2 | 4/2006 | Flaherty | |
| 7,098,803 B2 | 8/2006 | Mann et al. | |
| 7,109,878 B2 | 9/2006 | Mann et al. | |
| 7,123,964 B2 | 10/2006 | Betzold et al. | |
| 7,875,022 B2 * | 1/2011 | Wenger | A61M 5/14244 604/131 |
| 7,904,061 B1 * | 3/2011 | Zaffino | G11B 27/105 455/414.1 |
| 8,282,626 B2 * | 10/2012 | Wenger | A61M 5/14244 604/131 |
| 2001/0003542 A1 * | 6/2001 | Kita | 381/334 |
| 2002/0040208 A1 | 4/2002 | Flaherty et al. | |
| 2002/0046315 A1 * | 4/2002 | Miller | G06F 9/4443 711/1 |
| 2002/0164973 A1 * | 11/2002 | Janik | G11B 27/10 455/403 |
| 2003/0055380 A1 | 3/2003 | Flaherty | |
| 2003/0121055 A1 * | 6/2003 | Kaminski | H04N 5/76 725/115 |
| 2004/0010207 A1 | 1/2004 | Flaherty et al. | |
| 2004/0064088 A1 | 4/2004 | Gorman et al. | |
| 2004/0064096 A1 | 4/2004 | Flaherty et al. | |
| 2004/0078028 A1 | 4/2004 | Flaherty et al. | |
| 2004/0087894 A1 | 5/2004 | Flaherty | |
| 2004/0092865 A1 | 5/2004 | Flaherty et al. | |
| 2004/0092878 A1 | 5/2004 | Flaherty | |
| 2004/0116866 A1 | 6/2004 | Gorman et al. | |
| 2004/0127844 A1 | 7/2004 | Flaherty | |
| 2004/0153032 A1 | 8/2004 | Garribotto et al. | |
| 2004/0204673 A1 | 10/2004 | Flaherty | |
| 2004/0220551 A1 | 11/2004 | Flaherty et al. | |
| 2004/0235446 A1 | 11/2004 | Flaherty et al. | |
| 2004/0260233 A1 | 12/2004 | Garibotto et al. | |
| 2005/0010165 A1 * | 1/2005 | Hickle | A61B 5/417 604/66 |
| 2005/0021005 A1 | 1/2005 | Flaherty et al. | |
| 2005/0022274 A1 | 1/2005 | Campbell et al. | |
| 2005/0065760 A1 | 3/2005 | Murtfeldt et al. | |
| 2005/0090808 A1 | 4/2005 | Malave et al. | |
| 2005/0137530 A1 * | 6/2005 | Campbell et al. | 604/131 |
| 2005/0171512 A1 | 8/2005 | Flaherty | |
| 2005/0182366 A1 | 8/2005 | Vogt et al. | |
| 2005/0203461 A1 | 9/2005 | Flaherty et al. | |
| 2005/0215982 A1 | 9/2005 | Malave et al. | |
| 2005/0222645 A1 | 10/2005 | Malave et al. | |
| 2005/0238507 A1 | 10/2005 | DiIanni et al. | |
| 2006/0041229 A1 | 2/2006 | Garibotto et al. | |
| 2006/0042633 A1 | 3/2006 | Bishop et al. | |
| 2006/0074381 A1 | 4/2006 | Malave et al. | |
| 2006/0214511 A1 * | 9/2006 | Dayan | 307/38 |
| 2006/0258976 A1 * | 11/2006 | Shturman et al. | 604/22 |
| 2007/0073228 A1 | 3/2007 | Mernoe et al. | |
| 2007/0073235 A1 | 3/2007 | Estes et al. | |
| 2007/0073236 A1 | 3/2007 | Mernoe et al. | |
| 2007/0093786 A1 * | 4/2007 | Goldsmith et al. | 604/890.1 |
| 2007/0112298 A1 * | 5/2007 | Mueller et al. | 604/65 |
| 2007/0123819 A1 | 5/2007 | Mernoe et al. | |
| 2007/0124002 A1 | 5/2007 | Estes et al. | |
| 2007/0155307 A1 * | 7/2007 | Ng et al. | 455/3.01 |
| 2007/0167912 A1 | 7/2007 | Causey et al. | |
| 2007/0169607 A1 * | 7/2007 | Keller | G11B 17/22 84/1 |
| 2007/0179444 A1 | 8/2007 | Causey et al. | |
| 2007/0219480 A1 * | 9/2007 | Kamen | G05D 7/0647 604/20 |
| 2007/0248238 A1 * | 10/2007 | Abreu | G02C 3/003 381/381 |
| 2007/0255250 A1 | 11/2007 | Moberg et al. | |
| 2007/0287931 A1 * | 12/2007 | Dilorenzo | A61B 5/0476 600/545 |
| 2008/0015422 A1 * | 1/2008 | Wessel | A61B 5/14532 600/301 |
| 2008/0027574 A1 * | 1/2008 | Thomas | 700/94 |
| 2008/0031481 A1 | 2/2008 | Warren et al. | |
| 2008/0198012 A1 | 8/2008 | Kamen | |
| 2008/0300572 A1 | 12/2008 | Rankers et al. | |
| 2009/0076849 A1 | 3/2009 | Diller | |
| 2009/0177142 A1 * | 7/2009 | Blomquist et al. | 604/66 |
| 2009/0221890 A1 * | 9/2009 | Saffer et al. | 600/347 |
| 2010/0094078 A1 * | 4/2010 | Weston | A61M 1/06 600/27 |
| 2013/0159456 A1 * | 6/2013 | Daoud | H04L 67/12 709/217 |

FOREIGN PATENT DOCUMENTS

| | | |
|---|---|---|
| WO | WO 2005/072794 | 8/2005 |
| WO | WO 2006/105794 | 10/2006 |
| WO | WO 2007/005219 | 1/2007 |

OTHER PUBLICATIONS

European Patent Office, International Preliminary Report on Patentability for Application PCT/US2008/086239, dated Jun. 24, 2010, 13 pages.
International Search Report & Written Opinion PCT/US2006/036369, mailed Aug. 14, 2007, 16 pages.
International Search Report and Written Opinion, PCT/US2008/086239, mailed Oct. 2, 2009, 20 pages.
Invitation to Pay Fees, PCT/US2008/086239, mailed Jun. 18, 2009, 11 pages.
OmniPod Insulin Management System-Investor Relations—Press Release, Feb. 1, 2005, http://investors.insulet.com/phoenix.zhtml?c=209336&p=iroi-newsArticle&ID=988708&highlight= 1 page.
OmniPod Quick Start Guide, 2007, 2 pages.

(56) References Cited

OTHER PUBLICATIONS

The Medtronic Diabetes Connection, 2006, 6 pages.

Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.

* cited by examiner

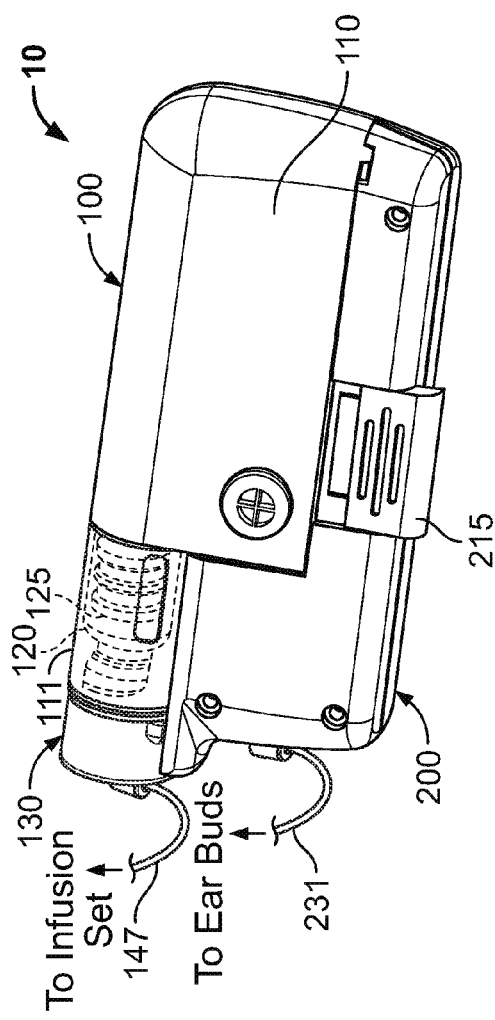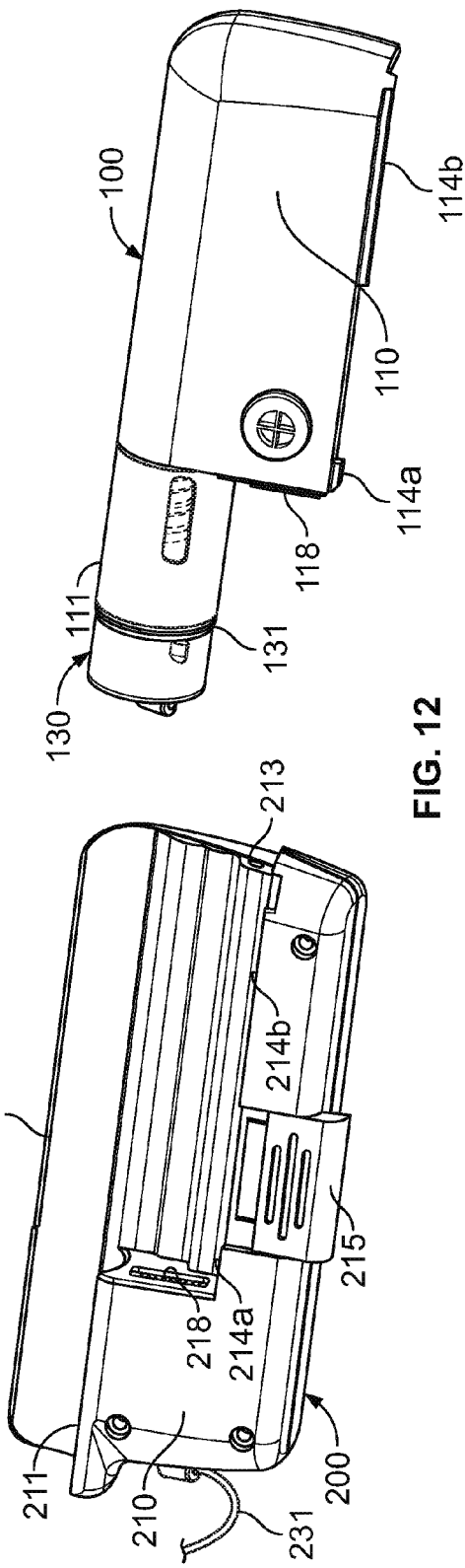

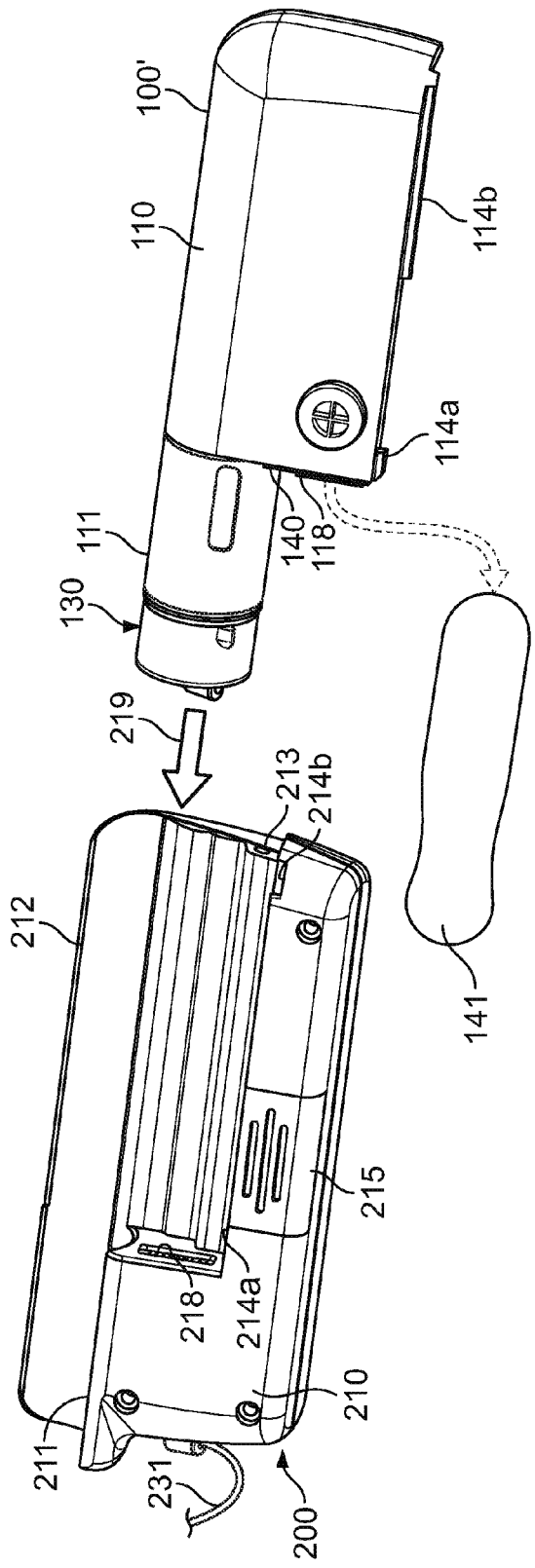

PORTABLE INFUSION PUMP AND MEDIA PLAYER

CROSS-REFERENCE TO RELATED APPLICATION(S)

This is a continuation of U.S. application Ser. No. 12/968,741 filed on Dec. 15, 2010 (now U.S. Pat. No. 8,282,626), which is a division application of U.S. application Ser. No. 11/954,755 filed on Dec. 12, 2007 (now U.S. Pat. No. 7,875,022), the contents of these previous applications are incorporated herein by reference.

TECHNICAL HELD

This document relates to portable infusion pump systems to deliver fluids, such as insulin infusion pumps or the like.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

SUMMARY

Some embodiments of a portable infusion pump system can be configured to deliver medicine (e.g., insulin or the like) to a user while also delivering media content to the user. The media content can include, for example, MP3 music data or other audio/video data stored in a memory device in the portable system. Thus, in particular embodiments, the portable infusion pump system can serve a dual purpose of providing medication and entertainment for the user from a compact and unobtrusive device. Moreover, the infusion pump system may be used to deliver alarms that alert the user when the pump system requires user action or acknowledgement. In such circumstances, the pump system can be configured to interrupt the music content or other media content in order to deliver the alarm via the user's listening device (e.g., earbuds, other headphone device, or the like), thereby enhancing safety where the user might otherwise miss the alarm.

In particular embodiments, a medical infusion pump system may include a portable housing defining a space to receive a medicine. The system may also include a pump drive system to dispense medicine to a user from the housing when the medicine is received in the space. Further, the system may include a controller that electrically communicates with the pump drive system to transmit activation signals to the pump drive system. The system may also include an external audio device that communicates with at least a portion of the controller. The controller may access digital music content stored in a memory device to output selected music through the external audio device to die user. Also, the controller may interrupt the selected music output through the external audio device to the user in response to a medicine dispensation alarm condition.

Some embodiments described herein include a method of operating a medical infusion pump system. The method may include activating a pump drive system of a portable infusion, pump system to dispense medicine to a user according to set parameters. Also, the method may include accessing digital music content stored in a memory device of the portable infusion pump system to output selected music through external audio device to the user. The method may further include, in response to a detected alarm condition of the portable infusion pump system, interrupting the selected music output through the external audio device to the user so as to deliver an audible alert through the external audio device.

In certain embodiments, a medical infusion pump system may include a portable housing defining a space to receive a medicine. The system may also include a pump drive system to dispense medicine to a user from the housing when the medicine is received in the space. The system may further include a controller that electrically communicates with the pump drive system to transmit activation signals to the pump drive system. The system may further include a media content playback system that communicates with at least a portion of the controller to output selected media content to the user. The controller may access instructional media content stored in a memory so device to output tutorial information through the media content playback system to the user. The tutorial information may communicate actions to be performed by the user of the medical infusion pump system.

In some embodiments, a medical infusion pump system may include a portable housing defining a space to receive a medicine, and a pump drive system to dispense medicine to a user from the housing when the medicine is received in the space. The system may also include a controller that electrically communicates activation signals to the pump drive system to control the dispensation of the medicine. The system may further include a media content playback system having an external audio device connectable to the controller so as to output selected media content to the user. The controller may access digital media content stored in a memory device to output selected media content through the external audio device to the user. The system may also include a user interface electrically coupled to the controller. The user interface may include a display device that contemporaneously displays medicinal delivery information and media content playback information.

Some embodiments described herein include a method of using a medical infusion pump system. The method may include actuating one or more buttons of a user interface of a portable infusion pump system so as to adjust a pump parameter. The portable infusion pump system may have a pump drive system to dispense medicine to a user according to the parameter. The method may also include actuating one or more buttons of the user interface to select media content for playback through an external audio device to the user. The selected media content may be stored with a plurality of digital media content files in a memory device of the portable infusion pump system. The method may further include contemporaneously receiving the medicine dispensed from the portable infusion pump system and receiving the playback of the selected media content output by the portable infusion pump system.

Some or all of the embodiments described herein may provide one or more of the following advantages. First, some embodiments of an infusion pump system can be capable of infusing medication (e.g., insulin or the like) to a user while also delivering audio or video media content to the user, thereby proving provide both medication infusion and entertainment output for the user. As such, there may be no need for the user to carry and operate a separate media playback device, thereby simplifying the process for selecting and receiving media playback and reducing the number of devices that must be carried, by the user. Second, the infusion pump system can be configured to be compact and unobtrusive device, which provides a system that is readily portable and wearable. Third, the user can contemporaneously monitor infusion pump operation and control the media content playback from the same user interface on the portable system. Fourth, in some embodiments, the pump system can be configured to interrupt the music content or other media content in order to deliver an alarm via the user's external audio device (e.g., earbud device, other headphone device, or the like), thereby enhancing the user safety. Fifth, the media content played by the pump system may include an audio tutorial or other instructional content on how to operate particular features of the pump system, which can facilitate new user training in a manner that is helpful for children or other users in need of further training outside of a clinic environment.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 11-12 are perspective views of a pump device being detached from a controller device, in accordance with some embodiments.

FIGS. 15-16 are perspective views of the new pump device of FIG. 13 being attached to the controller device of FIG. 13.

Like reference symbols in the various drawings indicate like elements.

DETAILED DESCRIPTION OF ILLUSTRATIVE EMBODIMENTS

Some embodiments of an infusion pump system can serve a dual purpose of providing medication and entertainment for the user from a compact and unobtrusive device. For example, an infusion pump system can be portable and wearable such that the system is capable of infusing medication (e.g., insulin or the like) to a user while also delivering digital audio/video media content to the user. In such circumstances, the pump system can interrupt the music content or other media content in order to deliver the alarm, via the user's earbuds or other headphone device, which enhances user safety where the user might otherwise miss the alarm. Also, the media content stored in, and output by, the pump system 10 may include an audio tutorial or other instructional content on how to operate particular features of the system, thereby facilitating new user training. As described in more detail below, particular embodiments of the infusion pump system may include a disposable pump device, and other embodiments may include a reusable pimp device.

Figure 1:
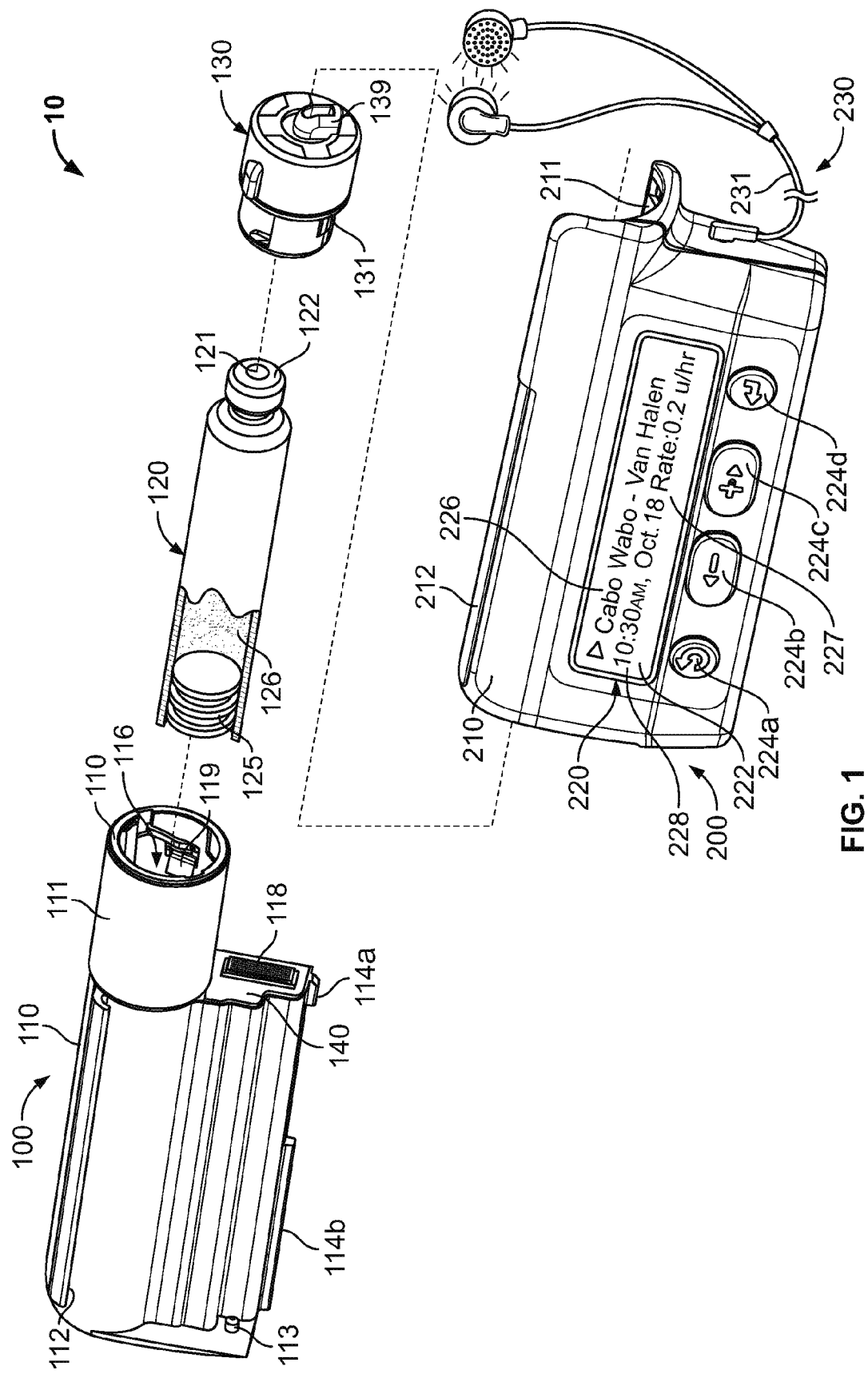
FIG. 1 is a perspective view of an infusion pump system in accordance with some embodiments.
Figure 2:
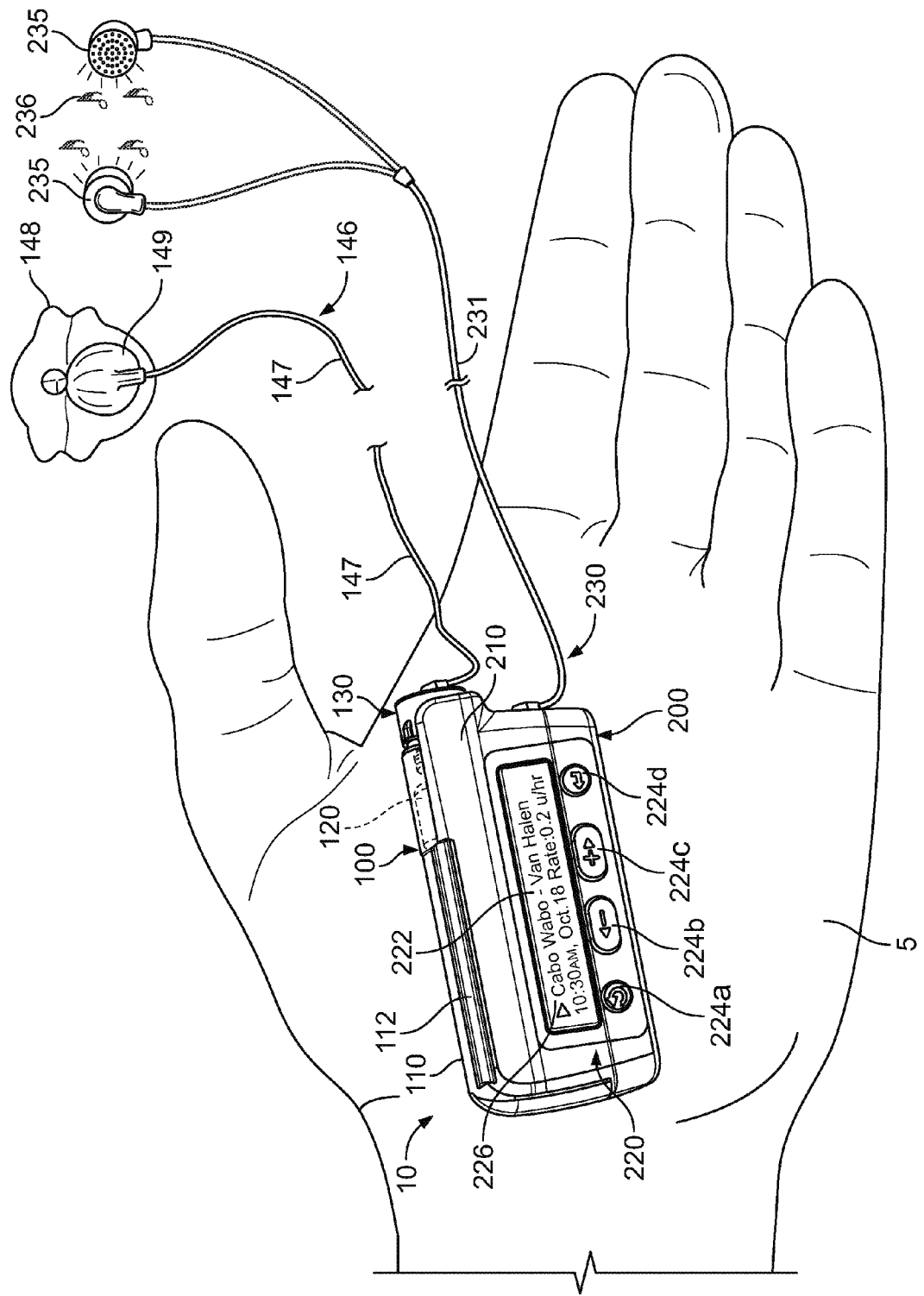
FIG. 2 is another perspective view of the infusion pump system of FIG. 1.
Figure 3:
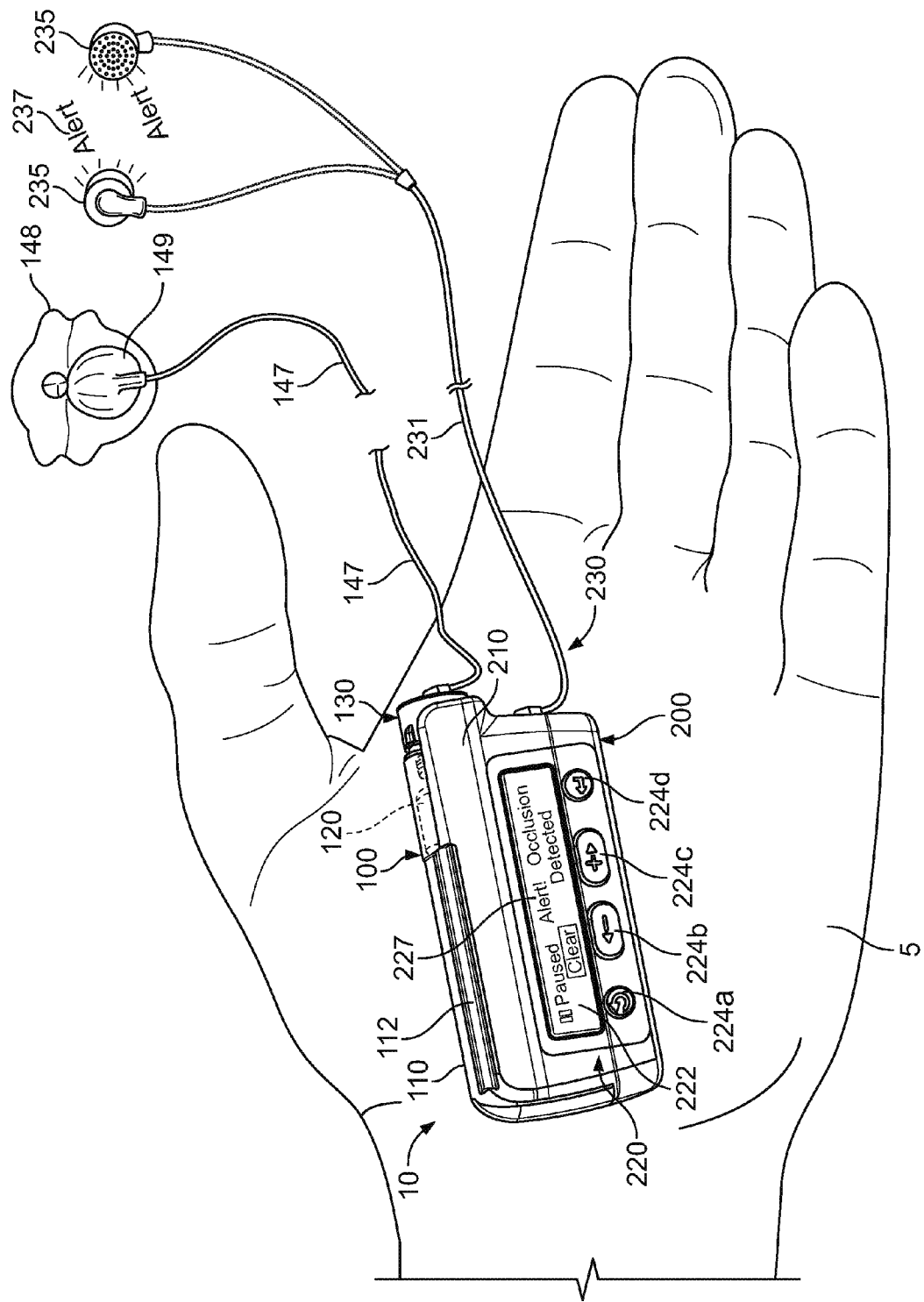
FIG. 3 is another perspective view of the infusion pump system of FIG. 1.

Referring now to FIGS. 1-3, some embodiments of an infusion pump system 10 can include a pump device 100 and a controller device 200 that can communicate with the pump device 100. The pump device 100 can include a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include as drive system (described in more detail below) that advances a plunger 125 in the fluid cartridge 120 so as to dispense fluid therefrom. The controller device 200 can communicate with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing or in the user's pocket while receiving the fluid dispensed from the pump device 100.

Figure 13:
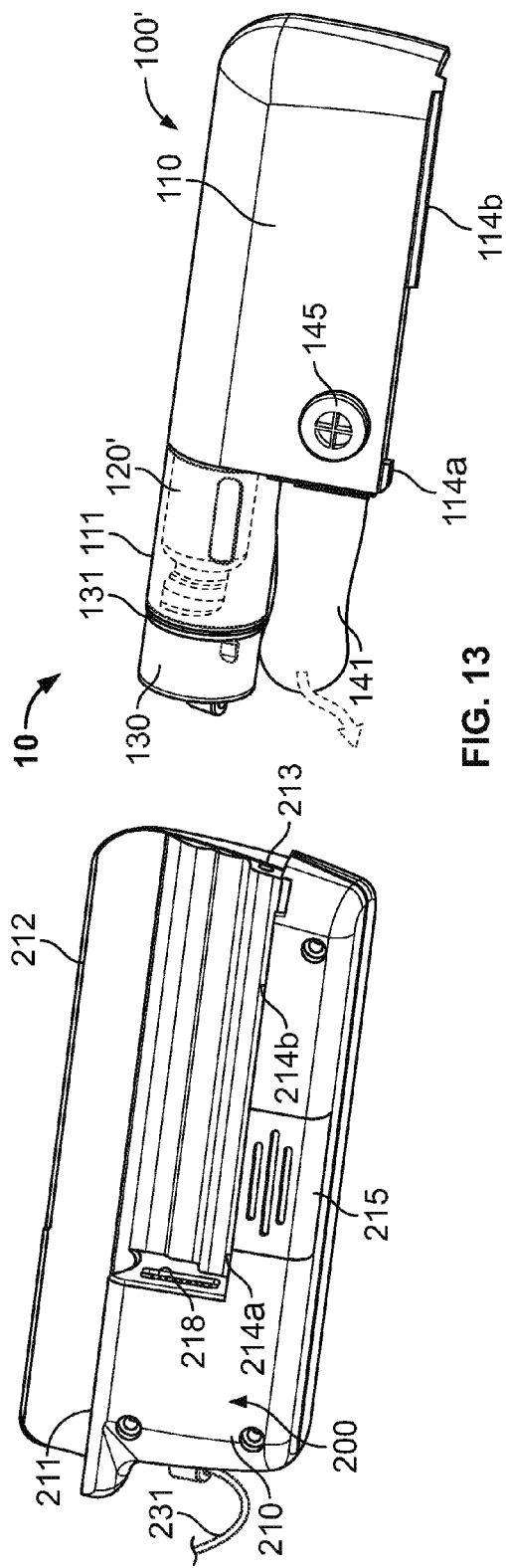
FIGS. 13-14 are perspective views of the pump device of FIGS. 11-12 being discarded and the controller device of FIGS. 11-12 being reused with a new pump device.

The controller device 200 may be configured as a reusable component that provides electronics and a user interface to control the operation of the pump device 100. In such circumstances, the pump device 100 can be a disposable component that is discarded after a single use. For example, as described in more detail below in connection with FIGS. 11-16, the pump device 100 can be a "one time use" component that is thrown away after the fluid cartridge 120 therein is exhausted. Thereafter, the user can removably attach a new pump device 100' (having a new medicine cartridge 120' as shown in FIG. 13) to the reusable controller device 200 for the dispensation of fluid from a new fluid cartridge 120'. Accordingly, the user is permitted to reuse the controller device 200 (which may include valuable electronics or data) while disposing of the relatively low-cost pump device 100 after each use. Such a pump system 10 can provide enhanced user safety as a new pump device 100 (and drive system therein) is employed with each new fluid cartridge 120.

Still referring to FIGS. 1-3, the infusion pump system 10 may also include an media content playback system 230 that can playback digital media content (e.g., music, voice instructions, audiobooks, audio that corresponds to a video being displayed, and other data) to the user while the pump system 10 is delivering the medicine to the user. The playback system 230 may comprise, for example, an external audio device 231 that plugs into a connection port 234 (refer to FIG. 17) so as to mate with an audio jack 232 housed by the controller device 200. Furthermore, the playback system 230 can output to the user media content that is electronically stored in one or more memory devices 246 (refer to FIG. 17) arranged in the controller device 200. Accordingly, the user can operate the infusion pump system 10 so as to receive controlled delivery of a medicine 126 while also viewing and/or listening to the playback of selected music, video, or other media content (e.g., playback of MP3, WMA, WMV, or DIVX Files). In such embodiments, the pump system 10 may provide a compact, multi-purpose device that eliminates the need for the user to carry multiple devices (e.g., a medical pump device and a separate media player device). Moreover, the infusion pump system 10 can enhance user safety by interrupting the music content or other media content in order to deliver an alarm to the user that might otherwise go unnoticed if the user was listening to a separate media player device.

Briefly, in use, the pump device 100 can be configured to be removably attached to the controller device 200 in a manner that provides a secure fitting, an overall compact size, and a reliable electrical connection that is resistant to water migration. For example, as described in more detail below in connection with FIGS. 11-16, the controller device 200 can include a housing 210 having a number of features that mate with complementary features of the pump housing 110. In such circumstances, the controller device 200 can be removably attached to the pump device 100 in a generally side-by-side configuration while not fully surrounding the pump housing 110. Accordingly, in this embodiments, the pump device 100 and the controller device 200 can be separate components that fit together, but the overall size of the combined assembly can be reduced because there is no requirement for one component (e.g., the controller device) to completely surround or envelop the second component (e.g., the pump device). The compact size permits the infusion pump system 10 to be discrete and portable (as described, below in connection with FIGS. 9-10). Moreover, at least one of the pump device 100 or the controller device 200 can include a release member that facilitates an easy-to-use detachment and replacement process.

Referring again to FIGS. 1-3, the pump system 10 can be a medical infusion pump system that is configured to controllably dispense a medicine from the cartridge 120. As such, the fluid cartridge 120 can contain a medicine 126 (FIG. 1) to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, as shown in FIG. 1, the pump housing structure 110 can include one or more retainer wings 119 that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings 119 interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. Accordingly, the pump device 100 can operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-3, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIGS. 1-3, refer to FIG. 18) of the pump device 100. As described in more detail below, the pump device 100 can include a drive system that causes controlled dispensation of the medicine or other fluid from the cartridge 120, hi some embodiments, the drive system incrementally advances a piston rod (not shown in FIGS. 1-3) longitudinally into the cartridge 120 so that the fluid is forced out of an output end 122. A septum 121 (FIG. 1) at the output end 122 of the fund cartridge 120 can be pierced to permit fluid outflow when the cap device 130 is connected to the pump housing structure 110 (described in more detail below). Thus, when the pump device 100 and the controller device 200 are attached and thereby electrically connected, the controller device 200 can communicate electronic control signals via a hardwire connection (e.g., electrical contacts or the like) to the drive system or other components of the pump device 100. In response to the electrical control signals from the controller device 200, the drive system of the pump device 100 causes medicine to incrementally dispense from the medicine cartridge 120.

As shown in FIG. 1, the pump device 100 can include an electrical connector 118 (e.g., having conductive pads, pins, and the like) that are exposed to the controller device 200 and that mate with a complementary electrical connector (refer to connector 218 in FIG. 8) on the adjacent face of the controller device 200. The electrical connectors 118 and 218 provide the electrical communication between the control circuitry (refer, for example, to FIG. 17) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. Furthermore, the infusion pump system 10 can include a gasket 140 that provides a seal around the electrical connector interface to thereby resist migration of external contaminants when the pump device 100 is attached to the controller device 200. Thus, in some embodiments, the infusion pump system 10 can be assembled into a water resistant configuration that protects the electrical interconnection from water migration (e.g., if the user encounters water while carrying the pump system 10).

Still referring to FIGS. 1-3, the controller device 200 can include a user interface 220 that permits a user to monitor the operation of the pump device 100. In some embodiments, the user interface 220 includes a display device 222 and one or more user-selectable buttons (e.g., four buttons 224a, 224b, 224c, and 224d in this embodiment). The display device 222 can include an active area in which numerals, text, symbols, images, or a combination thereof can be displayed (refer, for example, to FIG. 2). For example, the display device 222 can be used to communicate media content information 226, which may related to the selected media content that is being delivered to the user through the playback system 230. Also, the display device 222 can be used to communicate a number of settings or menu options for the infusion pump system 10. For example, the display device 222 can be used to communicate medicinal delivery information 227, such as the basal delivery rate (as shown in FIG. 1), a bolus dosage, a historical record of medicine delivered, the amount of medicine remaining in the cartridge 120, or the like. In another example, the display device 222 can be used to communicate time and date information 228, which can be used by the user to determine dosage schedules, bolus delivery times, meal times, or the like.

In this embodiment, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 128, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time. Accordingly, when the controller device 200 is connected to the pump device 100, the user can be provided with the opportunity to readily monitor infusion pump operation by simply viewing the user interface 220 of the controller device 200 connected to the pump device 180. Such monitoring capabilities may provide comfort to a user who may have urgent questions about the current operation of the pump device 100. Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine) the user can readily operate the user interface 220 of the controller device 200, which is removably attached to the pump device 100, without the requirement of locating and operating a separate monitoring module.

In another example, the user can press one or more of the buttons 224a, 224b, 224c, and 224d of the user interface 220 to play, pause, rewind, or fast-forward the selected media content 226 or to otherwise control the output of media cement through the playback system 230. Thus, when the controller device 200 is connected to the pump device 100, the user can contemporaneously monitor infusion pump operation and control the media content playback from the same user interface 220. Again, in these embodiments, there may be no need for the user to carry and operate a separate media playback device, thereby simplifying the process for selecting and receiving media playback and reducing the number of devices that must be carried by the user. Furthermore, in some embodiments, the pump system 10 can be configured to interrupt the music content or other media content in order to deliver an alarm via the user's external audio device 231 (e.g., earbud device, other headphone device, or the like), thereby enhancing the user safety. Finally, the media content played by the pump system 10 may include an audio tutorial or other instructional content on how to operate particular features of the system, which facilitates new user training (especially for children or other young users).

Referring to now FIGS. 2-3, the infusion pump system 10 may be configured to be portable so that the user can readily carry or wear the pump system during operation. For example, a user can conveniently wear the infusion pump system 10 on the user's skin (e.g., skin adhesive) underneath the user's clothing or carry the pump device 100 in the user's pocket (or other portable location) while both receiving the medicine dispensed from the pump device 100 and receiving the playback of the selected media content. As described below in connection with FIG. 18, the drive system of the pump device 100 may be arranged in a compact manner so that the pump device 100 has a reduced length. For example, in the circumstances in which the medicine cartridge 120 has a length of about 6 cm to about 7 cm (about 6.4 cm in one embodiment), the overall length of the pump housing structure 110 (which contains medicine cartridge and the drive system) can be about 7 cm to about 10 cm and about 7 cm to about 9 cm (about 8.3 cm or less in one embodiment). In addition, the pump housing structure 110 may have an overall height of about 2 cm to about 4 cm (about 3.1 cm or less in one embodiment) and an overall thickness of about 8 mm to about 20 mm (about 17.5 mm or less in one embodiment). In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump system 10 (including the removable controller device 200 attached to the pump device 100 having the cap 130) may have an overall length of about 7 cm to about 10 cm (about 9.3 cm or less in one embodiment), an overall height of about 2 cm to about 5 cm (about 4.2 cm or less in one embodiment), and an overall thickness of about 8 mm to about 20 mm (about 17.5 mm or less in one embodiment).

The pump system 10 is shown in FIGS. 2-3 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) and receive the playback of the selected media content without the need for carrying and operating a separate module. In such embodiments, the pump device 100 can deliver the medicine 126 through an infusion set 146, and the controller device can deliver the selected, media content through the external audio device 231.

The infusion set 146 includes tubing system that connects the infusion pump system 10 to the tissue or vasculature of the user (e.g., to deliver medicine into the tissue or vasculature under the user's skin). The infusion set 146 may include a flexible tube 147 that extends from the pump device 100 to a subcutaneous cannula 149 retained by a skin adhesive patch 148 that secures the subcutaneous cannula 149 to the infusion site. The skin adhesive patch 148 can retain the infusion cannula 149 in fluid communication with the tissue or vasculature of the patient so that the medicine dispensed through the tube 147 passes through the cannula 149 and into the user's body. The cap device 130 may provide fluid communication between the output end 122 (FIG. 1) of the medicine cartridge 120 and the tube 147 of the infusion set 146. For example, the tube 147 may be directly connected to the output port 139 (FIG. 1) of the cap device 130. In another example, the infusion set 146 may include a connector (e.g., a Leur connector or the like) attached to the tube 147, and the connector can then mate with the cap device 130 to provide the fluid communication to the tube 147. In these examples, the user can carry the portable infusion pump system 10 (e.g., in the user's pocket, connected to a belt clip, adhered to the user's skin, or the like) while the tube 147 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

Still referring to FIGS. 2-3, the external audio device 231 can include one or more earbuds 235 that fit with the user's ear so as to direct the audio content into the ear for personal listening. The external audio device 231 can be used to deliver selected audio content 236 (refer to FIG. 2) for the user's listening enjoyment, but may also be used to interrupt the selected audio content to deliver an audible alert 237 (refer to FIG. 3) that notifies the user of a warning or condition related to the medicine delivery of the pump system 10. For example, the user can operate the user interface 220 of the controller device 200 so that the selected music content 236 is output through the earbuds 235 to the user's ear. The media content information 226 can be shown in the display device 222 of the pump system it) to indicate that the selected media content is now playing (refer, for example, to the "now playing" triangle symbol adjacent to the information 226 indicating the song title and artist as shown in FIG. 2). This may occur while the pump system is also operating to deliver controlled dosages of the medicine 126 to the user via the infusion set 146.

In the event that an alarm condition low power, low medicine volume, occlusion detection, drive system or electrical communication error, or the like) is detected by the pump system 10, one or both of the external audio device 231 and the display device 222 can be used to communicate an alert 237 to the user. For example, as shown in FIG. 3, if the pump system 10 detects an occlusion in the medicine flow path (which can cause inaccurate dosage delivery), an audible alert 237 can be used to interrupt the playback of the music content 236 (FIG. 2) and notify the user of the detected occlusion. The audible alert 237 may be in the form of an alert beep, a voice notification, or a combination thereof. In particular embodiments, the audible alert 237 can include a voice notification that states: "Alert. An occlusion has been detected. Please check the infusion set for blockages." in addition, the display device 222 of the controller 200 can be used to indicate that the music content 236 (FIG. 2) has been interrupted due to the detection of an alarm condition. For example, the display device 222 can indicate that the media content has automatically switched to a paused or stopped condition (refer, for example, to FIG. 3 which shows the "paused" symbol in the area formerly occupied by the media content information 226). Also, the display device 222 may provide a visual alert 227 that indicates the detected alarm condition.

In some circumstances, the playback of the media content may resume after the alert 237 (FIG. 3) has been communicated. For example, some alarm conditions may not require immediate intervention on the part of the user (e.g., a warning that the medicine cartridge 120 is 80% exhausted). Accordingly, the alert 237 may temporarily interrupt the music content 236 before the controller device 200 automatically resumes the is playback of the music content. In other circumstances, the playback of the media content may remain in the paused state until the user acknowledges receipt of the alarm communication. For example, as shown in FIG. 3, the user can acknowledge the alarm communication by pressing the button 224b adjacent to the "clear" command. Other alarm conditions may require further intervention by the user. In those situations, the audible alert 237 may include voice instructions that indicate the actions to be performed by the user.

Figure 4:
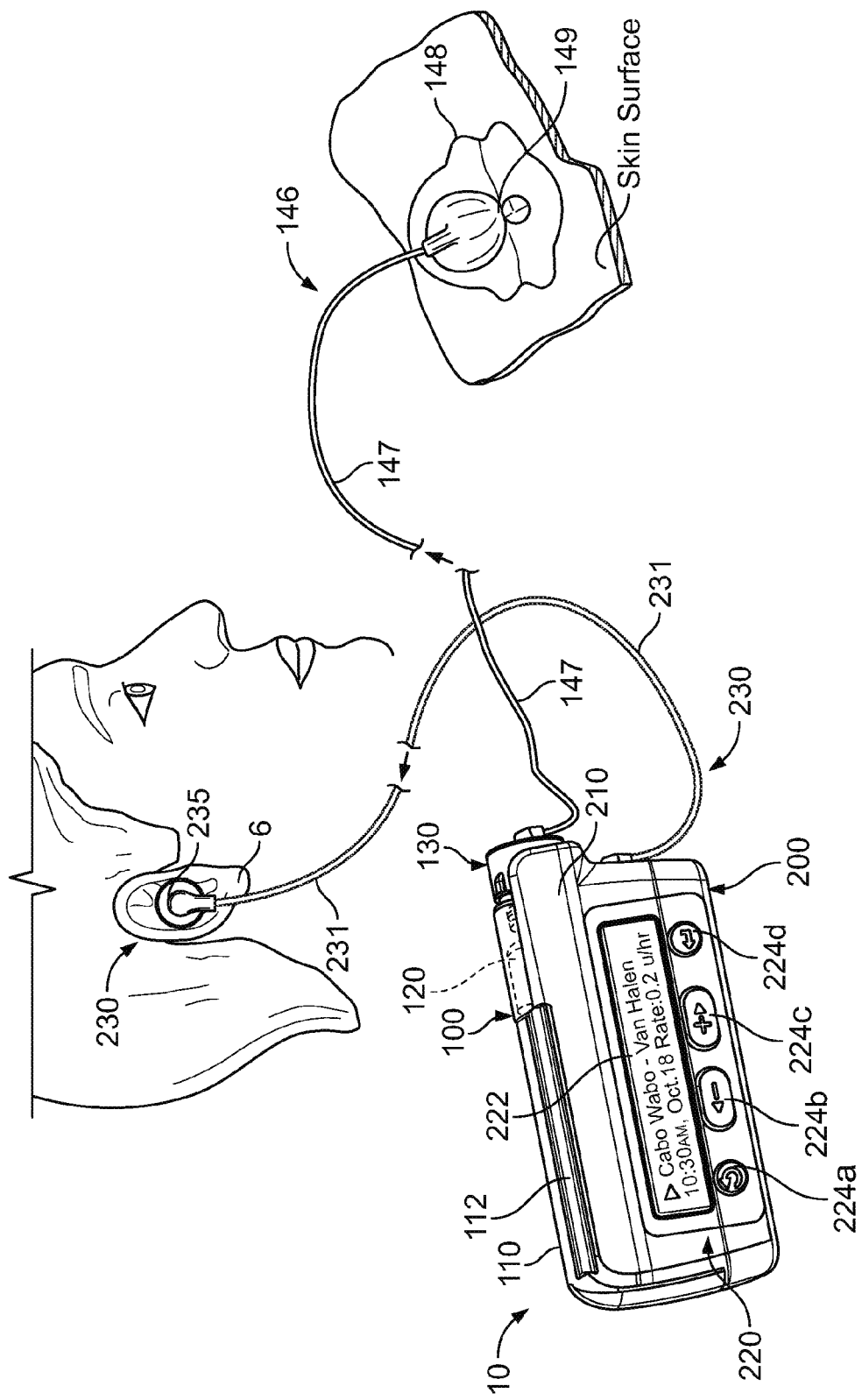
FIG. 4 is a perspective view of an infusion pump system in accordance with some embodiments.
Figure 5:
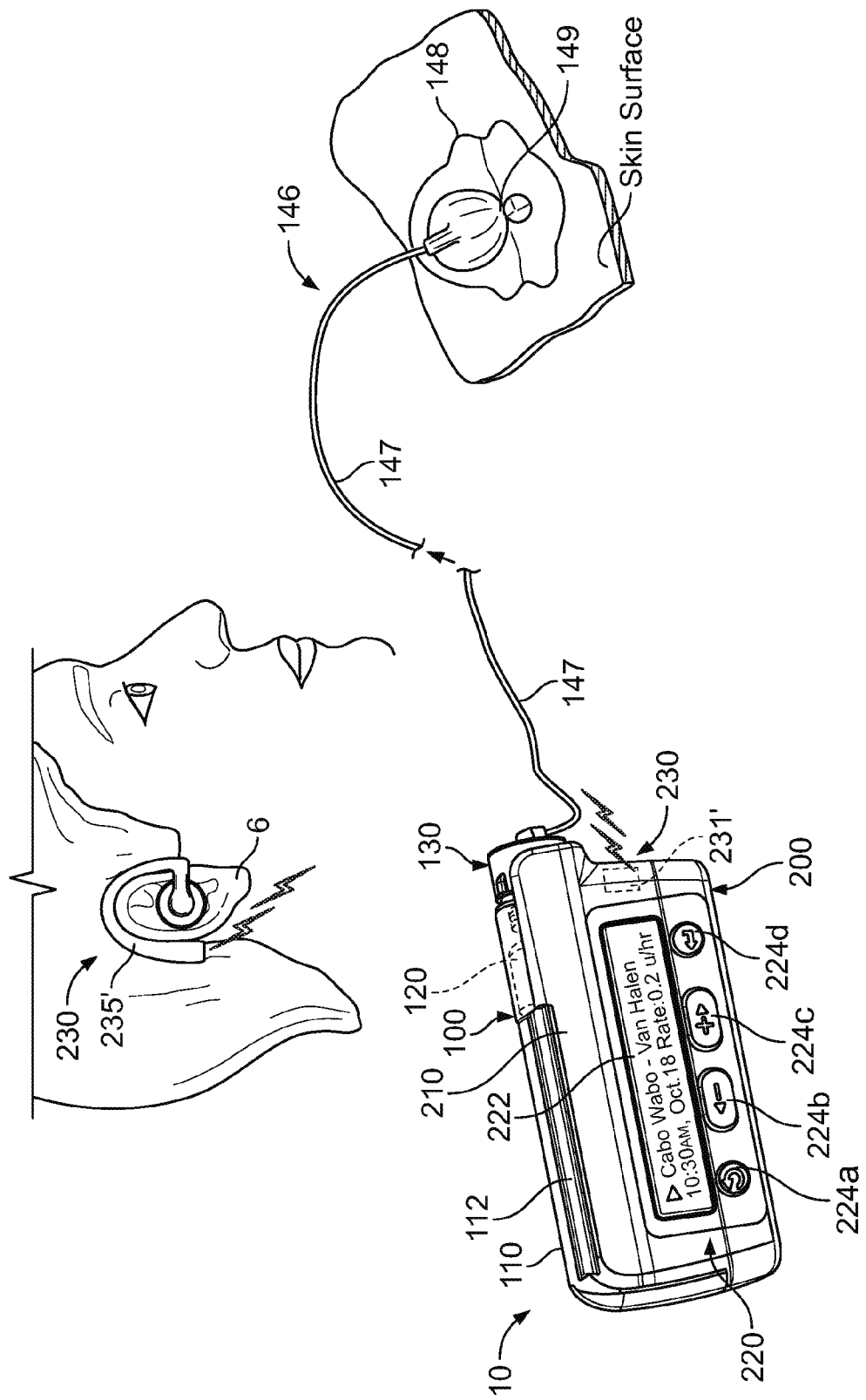
FIG. 5 is a perspective view of an infusion pump system in accordance with particular embodiments.

Referring new to FIGS. 4-5, the media content playback system 230 can deliver the selected, media content to the user via a hardwired connection to the external audio device 231 (FIG. 4) or a wireless link to at least one body-worn earpiece 235' (FIG. 5). As previously described, the infusion pump system 10 can be worn by the user (e.g., in the user's pocket, connected to a belt clip, adhered to the user's skin, or the like) while delivering playback of the selected media content to the user's ear 6. Thus, as shown in FIGS. 4-5, the pump system 10 can deliver the medicine 126 through the infusion set 146 adhered to the user's skin surface while contemporaneously outputting music content or other audio content to the user's ear 6.

In the embodiment depicted in FIG. 4, the external audio device 231 comprises a cable connection between the earbuds 235 and the audio jack 232 (FIG. 17) housed in the controller device 200. Accordingly, the user can arrange the pump system 10 so that the tubing 147 of the infusion set 146 extends from the pump device 100 to a targeted location on the user's skin and the cable of the external audio device 231 extends from the controller device 200 to the user's ear 6.

Figure 17:
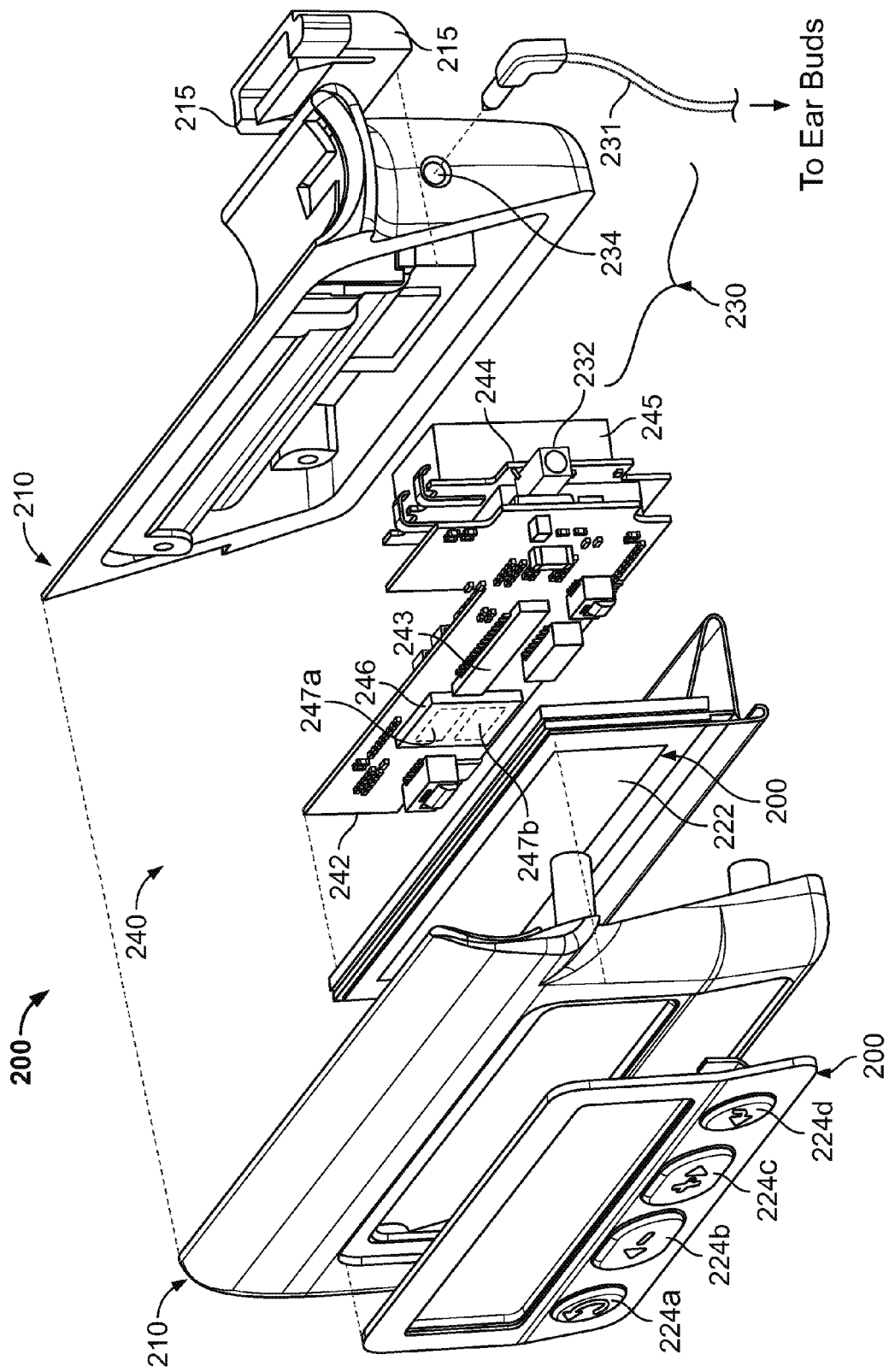
FIG. 17 is an exploded perspective view of a controller device for an infusion pump system, in accordance with some embodiments.

In alternative embodiments, the playback system 230 can include a wireless link to the earpiece so as to eliminate the audio cable extending from the pump system 10. For example, in the embodiment depicted in FIG. 5, the playback system 230 can include a wireless transmitter 231' that communicates media content data to a wireless earpiece device 235'. The media content transmitter 231' can output short-range signals (e.g., Bluetooth signals, RF signals, or the like) indicative of the audio content that is to be output from the speaker in the earpiece 235'. In this embodiment, the transmitter 231' is housed in the controller device 200 and is electrically connected to the control circuitry 240 therein (FIG. 17). The earpiece 235' can include an antenna and a wireless receiver arranged, for example, in a body-worn housing that is shaped to rest on the user's ear. As such, the wireless signals from the transmitter 231' are received by the earpiece 235's to thereby output the audio content into the user's ear 6. As previously described, the user can arrange the pump system 10 so that the tubing 147 of the infusion set 146 extends from the pump device 100 to a targeted location on the user's skin. However, in this embodiment, the user need not arrange the pump system 10 in a manner that accounts for an audio cable extending from pump system 10 because the earpiece 235' can receive the audio content information via the wireless link.

Figure 6:
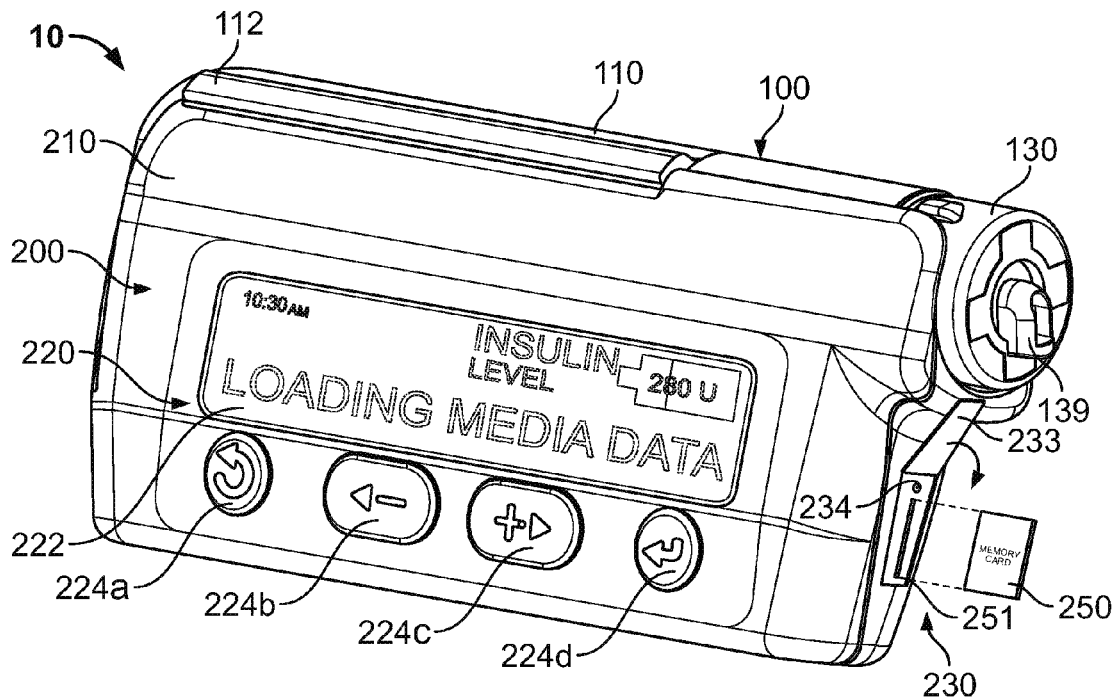
FIG. 6 is a perspective view of an infusion pump system that receives a removable memory device, in accordance with some embodiments.

Referring now to FIG. 6, some embodiments of the playback system 230 can operate with a removable memory card 250 that stores one or more media content files thereon. For example, the user may store a number of MP3 music files on the memory card 250 using a personal computer (not shown in FIG. 6) and then insert the memory card 250 into a corresponding port 251 of the playback system 230. As such, the playback system 230 can retrieve the media content data stored on the memory card in order to playback the media content to the user. Similar to previously described embodiments, the playback system 230 includes a connection port 234 that is configured to receive a cable of an external audio device 231 (FIGS. 1-3). Thus, the media content stored on the memory card 250 can be decoded or otherwise processed (e.g., by one or more components of the control circuitry 240 describe din connection with FIG. 17) so that the playback system 230 delivers the audio content to the earbuds or other speaker instrument of the external audio device 231.

The controller device 200 can include a protective cover 233 that can fit over at least one or the connection port 234 and the memory card port 251 of the playback system 230. The protective cover 233 is adjustable between an opened position (shown in FIG. 6) and a closed position in which the connection port 234 and the memory card port 251 are covered. The cover 233 may comprise a polymer material that serves to protect ports 234 and 251 from external contaminants when the cover 233 is in the closed position. For example, the cover 233 can comprise a flexible elastomers material that fits snugly in a depression over the ports 234 and 251, thereby enabling the cover to provide a water resistant structure over the ports 234 and 251.

Figure 7:
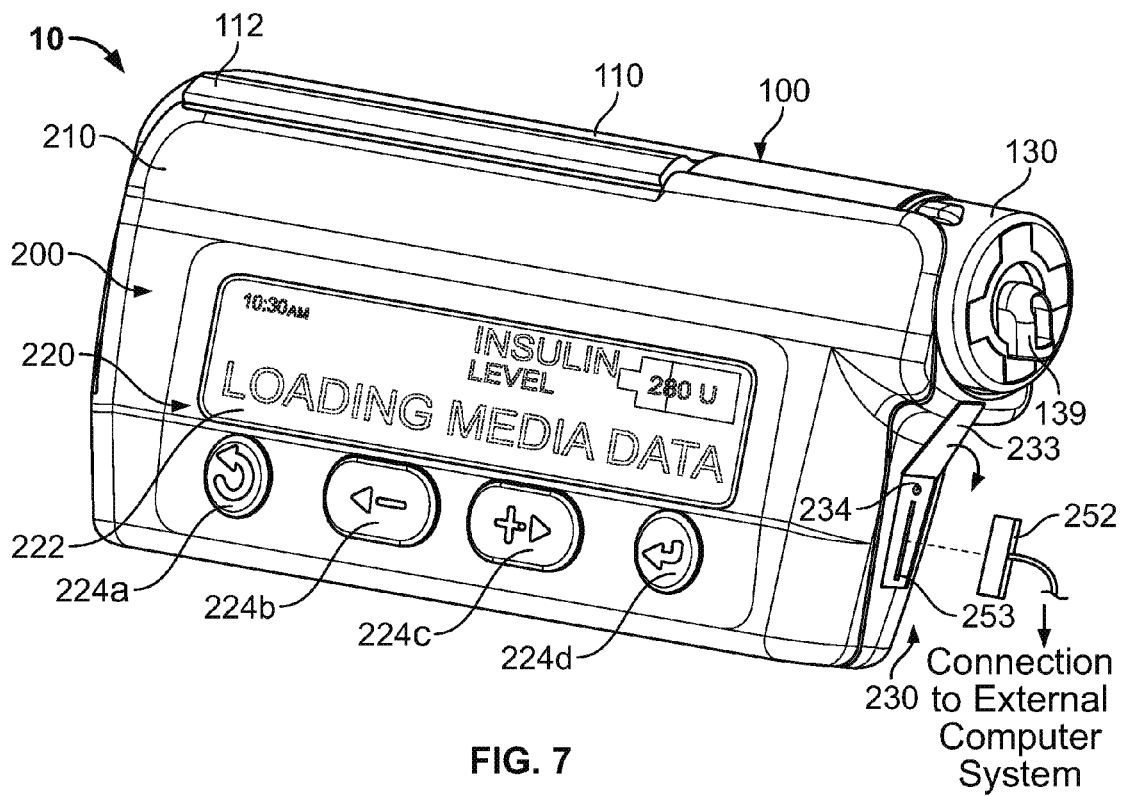
FIG. 7 is a perspective view of an infusion pump system that receives a computer interface cable, in accordance with some embodiments.

Referring now to FIG. 7, some embodiments of the playback system 230 can operate with a removable data cable 252 that communicates one or more media content files from a separate computer system. For example, the user may store a number of MP3 music files on a personal computer (not shown in FIG. 7), and the user can connect the data cable 252 with, a corresponding port 253 of the playback system 230 to transfer some or all of the MP3 files to an internal memory device (refer to memory device 246 in FIG. 17). In these circumstances, the user can periodically update or change the media content that is stored by the pump system and made available through the playback system 230. The playback system 230 can retrieve the media content data stored on the internal memory device in order to playback the media content to the user. Similar to previously described embodiments, the playback system 230 includes a connection port 234 that is configured to receive a cable of an external audio device 231 (FIGS. 1-3). Thus, the media content stored on the internal memory device can be decoded or otherwise processed so that the playback system 230 delivers the audio content to the earbuds or other speaker instrument of the external audio device 231. Also, in this embodiment, the controller device 200 can include the protective cover 233 to fit over at least one or the connection port 234 and the data cable port 253 of the playback system 230. As previously described, the protective cover 233 is adjustable between an opened position and a dosed position in which the connection port 234 and the memory card port 251 are covered. The cover 233 may comprise a polymer material that serves to protect ports 234 and 251 from external contaminants when the cover 233 is in the closed position.

Figure 8:
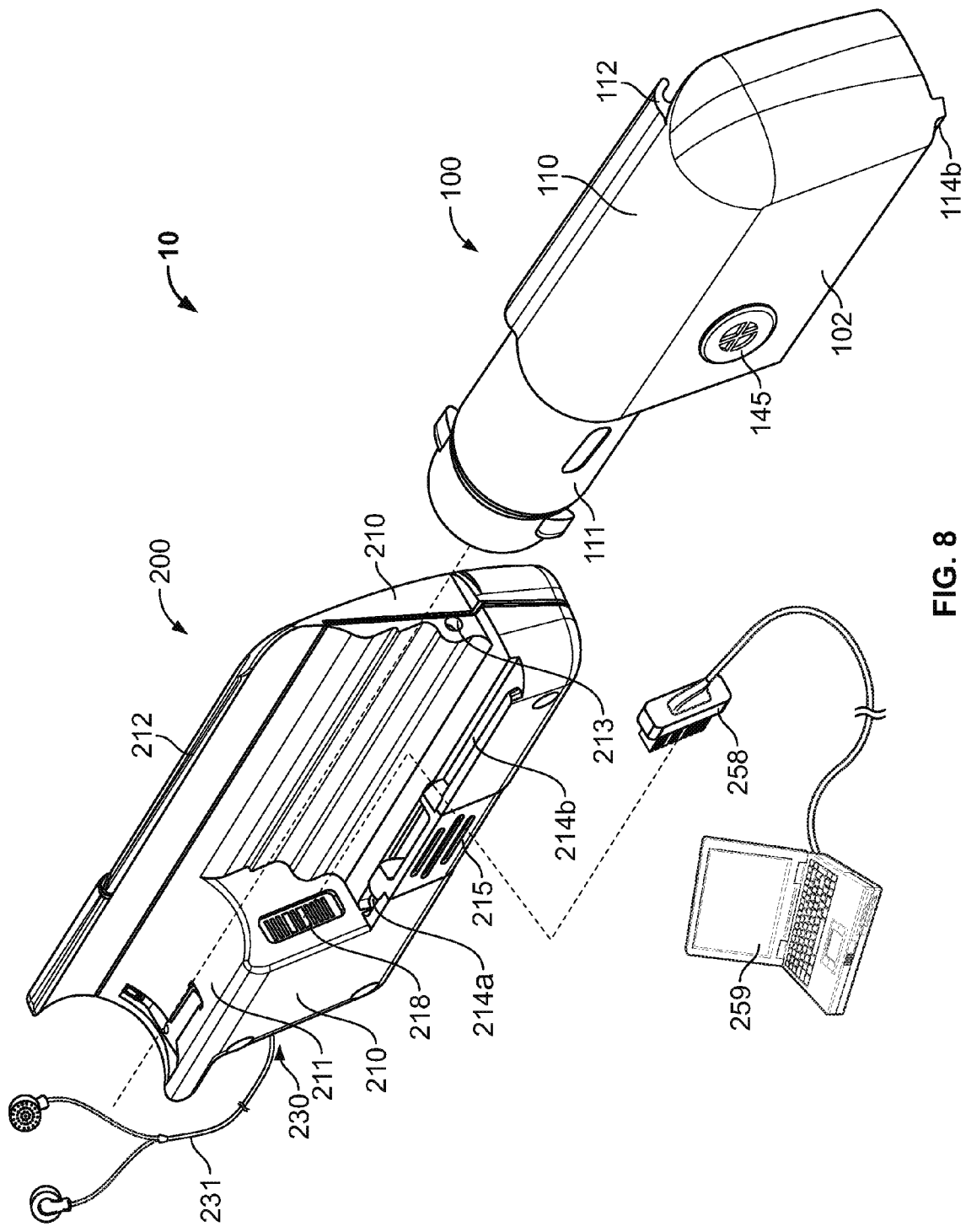
FIG. 8 is a perspective view of an infusion pump system that receives another computer interface cable, in accordance with certain embodiments.

Referring now to FIG. 8, some embodiments of the controller device 200 can be configured to receive media content files via a data cable connection with same electrical connector 218 that is capable of mating with the pump device 100. For example, the removable data cable 258 can transmit one or more media content files to the controller device 200 from a separate computer system 259. In such circumstances, the user may store a number of MP3 music files on a separate computer system 259, and the user can connect the data cable 258 with the electrical connector 218 to transfer some or all of the MP3 files to an internal memory device of the controller device 200 (refer to memory device 246 in FIG. 17). Thus, the user can periodically update or change the media content that is stored by the pump system 10 and made available through the playback system 230. The playback system 230 can retrieve the media content data stored on the internal memory device in order to playback the media content to the user via the external audio device 231.

As shown in FIG. 8, the data cable 258 can mate with the electrical connector 218 when the controller device is separated from the pump device 100. In the depicted embodiment, the controller device 200 is configured to be a reusable module that operates with a series of disposable pump devices 100 over a period of time. Accordingly after the data cable 258 transfers the selected, media content to the internal memory of the controller device 200, the data cable 258 can be disconnected to prepare the controller device 200 for attachment with the pump device 100. The pump device 100 can be configured to be removably attached to the controller device 200 in a manner that provides a secure fitting, an overall compact size, and a reliable electrical connection that is resistant to water migration.

In this embodiment, the pump device 100 may be moved in a longitudinal direction toward the controller device 200 until one or more structure connect and secure the separate components in the side-by-side arrangement. For example, the controller device 200 includes a controller housing structure 210 having a number of features that are configured to mate with complementary features of the pump housing structure 110 so as to form a releasable mechanical connection. In the embodiment shown in FIG. 8, the pump housing structure 110 includes a barrel 111 that mates with a complementary barrel channel 211 of the controller housing 210. Also, the pump housing 110 includes slider channel 112 that slidably engages a complementary rail 212 defined by the controller housing 210. The slider channel 112 can guide the relative motion between the pump device 100 and the controller device 200 in the longitudinal direction during the attachment process. Similarly, the pump housing 110 may include a segmented rail 114a-b (FIG. 1) that mates with a guide channel 214a-b to direct the relative longitudinal motion between the pump device 100 and the controller device 200. As described in more detail below, the segmented rails 114a-b may interact with the release member 215 so as to releasably secure the pump device 100 into assembly with the controller device 200. In addition, the pump housing 110 may include an extension 113 (FIG. 1) that mates with a depression 213 (FIG. 5) in the controller housing 210 when the pump device 100 is fully attached to the controller device 200.

Still referring to FIG. 8, when the pump device 100 is advanced in the longitudinal direction toward the controller device 200 as guided by the slider channel 112 and the segmented rails 114a-b, the electrical connector 118 (FIG. 1) of the pump device 100 is directed toward engagement with the mating connector 218 (FIG. 8) of the controller device 200. As the connectors 118 and 218 join together to form the electrical connection, the release member 215 is shifted to a position between the segmented rails 114a-b so as to prevent withdrawal of the connection. Also, when the connectors 118 and 218 are mated, the extension 113 and barrel 111 are mated with the corresponding depression 213 and barrel channel 211 so as to resist relative rotational movement between the pump device 100 and the controller device 200. In this embodiment, the physical attachment of the electrical connectors 118 and 218 may also serve to resist relative rotational movement between the pump device 100 and the controller device 200. Furthermore, when the connectors 118 and 218 are mated, the slide channel 112 is mated with the corresponding rail 112 and barrel channel 211 so as to resist relative side-to-side movement between the pump device 100 and the controller device 200.

Also, when the connectors 118 and 218 join together to form the electrical connection, the gasket 140 is compressed between the adjacent surfaces of the pump housing 110 and the controller housing 210. The gasket 140 may comprise a polymer foam material that is adhered to a surface of either the pump housing 110 or the controller housing 210 (e.g., adhered to the pump housing 110 in this embodiment). The gasket 140 may be die cut to a selected shape so as to include an aperture for the electrical connection. Thus, in this embodiment, the gasket 140 surrounds the electrical connection when the pump device 100 is secured to the controller device 200. The configuration provides protection from water migration to one or both of the electrical connectors 118 and 218. Accordingly, in particular circumstances, the infusion pump system 10 can be assembled into a "water tight" configuration that protects sensitive internal components from water migration in the event that the user encounters water while wearing the pump system 10.

Accordingly, the pump device 100 is configured to removably attach to the controller device 200 in a manner that provides a secure fitting, an overall compact size, and a reliable electrical connection. When the pump device 100 and the controller device 200 are arranged in this side-by-side configuration, the controller device 200 can be electrically connected with the pump device 100 while the controller device 200 remains outside of the pump housing 110 (and, likewise, the pump device 100 remains outside of the controller housing 210). As such, the overall size of the assembled system 10 can be minimized, thereby providing an infusion pump system 10 having a discrete size and enhanced portability.

Additionally, in some embodiments, the attachment of the pump device 100 to the controller device 200 can be accomplished by a user with a convenient "one-movement" process. For example, as previously described, the user can readily slide the pump device 100 and the controller device 200 toward one another in a single movement (e.g., in the longitudinal direction) that causes both a physical connection and an electrical connection. As described in more detail below in connection with FIGS. 11-16, the release member 215 may be arranged so as to automatically adjust to a locked position when the pump device 100 is advanced into engagement with the controller device 200. Thus, the infusion pump system 10 permits users to readily join the pump device 100 and the controller device 200 without compound or otherwise difficult band movements—a feature that can be beneficial to child users or to elderly users.

It should be understood that, in other embodiments, other features or connector devices can be used to facilitate the side-by-side mounting arrangement. These other features or connector devices may include, for example, magnetic attachment device, mating tongues and grooves, mounting protrusions that friction fit into mating cavities, or the like.

Figure 9:
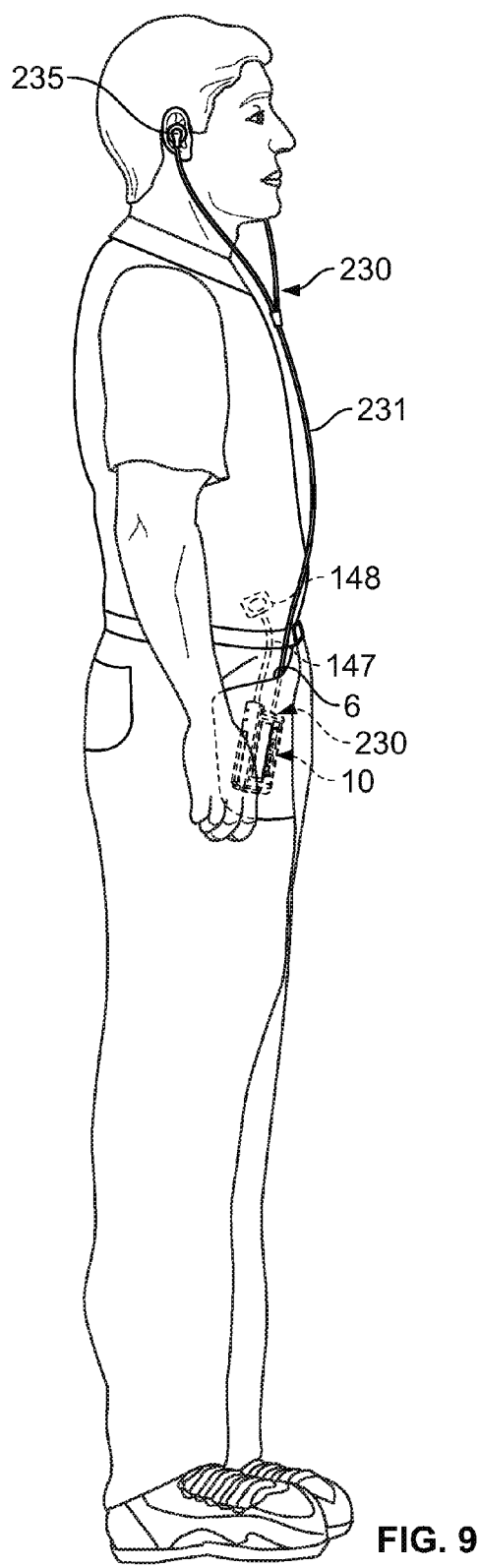
FIG. 9 is a perspective view of the infusion pump system worn on clothing of a user, in accordance with some embodiments.
Figure 10:
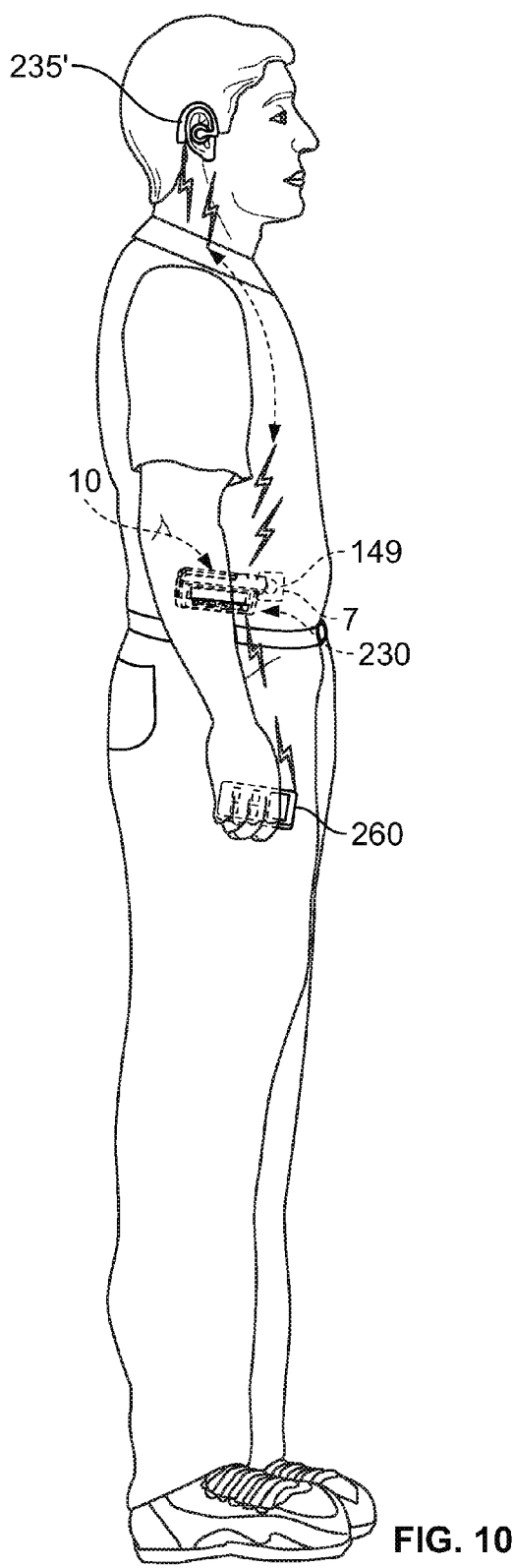
FIG. 10 is a perspective view of an infusion pump system worn on skin of a user, in accordance with particular embodiments.

Referring now to FIG. 9-10, a user can conveniently we the infusion pump system 10 on the user's skin (e.g., skin adhesive) underneath the user's clothing or carry the pump device 100 in the user's pocket or other portable location) while receiving both the medicine dispensed from the pump device 100 and the media content from the playback system 230. As previously described, in some embodiments the user can receive the media content via an audio cable of an external audio device 231 (FIG. 9), and in alternative embodiments the user can receive the media content via a wireless link to an earpiece device 235' (FIG. 10).

Referring to FIG. 9, in some embodiments, the infusion pump system 10 is pocket-sized so that the pump device 100 and controller device 200 can be worn in the user's pocket 6 or in another portion of the user's clothing. For example, the pump device 100 and the controller device 200 can be attached together and form the system 10 that comfortably fits into a user's pocket 6. The user can carry the portable infusion pump system 10 and use the tube 147 of the infusion set 146 to direct the dispensed medicine to the desired infusion site. In some circumstances, the user may desire to wear the pump system 10 in a more discrete manner. Accordingly, the user may pass the tube 147 from the pocket 6, under the user's clothing, and to the infusion site where the adhesive patch 148 is positioned. As such, the pump system 10 can be used to delivery medicine to the tissues or vasculature of the user in a portable, concealable, and discrete manner. Moreover, the pump system 10 in this embodiment includes the external audio device 231 having earbuds 235 that connect to the controller device 200 via the audio cable. In this embodiment, the audio cable of the external audio device 231 can extend out of the user's pocket 6 along the outside of the user's clothing. As such, the user can readily insert and remove the earbuds depending upon the user's preference at that particular time.

Referring to FIG. 10, in other embodiments, the infusion pump system 10 may be configured to adhere to the user's skin 7 directly at the location in which the skin is penetrated for medicine infusion. For example, a rear surface 102 (FIG. 3) of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 149 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220.

In the embodiments in which the pump system 10 is adhered to the user's skin under his or her clothing, the playback system 230 can include a wireless communication link to the earpiece device 235' (previously described in connection with FIG. 5). As such, the user can listen to music or other audio content stored in the pump system 10 without an audio cable that extends under his or her clothing to the pump system 10. Also, in some embodiments, the user can operate a remote control device 260 to control the playback of media content through the playback system 230. The remote control device 260 can be a portable module that fits in the user's hand or pocket. In this embodiment, the remote control device 260 includes a display screen and a plurality of buttons. The display screen can be used to indicate the media content information 226 (FIG. 1) related to the selected media content that is currently playing. The user can actuate the buttons of the remote control 260 to wirelessly control the playback of the media content stored in the pump system 10 (and output to the user via the playback system 230). For example, the user can operate the remote control device 260 to select a different song, adjust the playback volume, pause or resume the playback, and other such operations. Again, the remote control device 260 can be implemented in the embodiments in which the pump system 10 is adhered to the user's skin so that the user can control the playback of music or other audio content stored in the pump system 10 under his or her clothing.

Referring now to FIGS. 11-16, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some so embodiments, the controller device 200 may be designed to have an expected operational life of about 1 year to about 7 years, about 2 years to about 6 years, or about 3 years to about 5 years depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 11-12, the pump device 100 can be readily removed from the controller device 200 when the medicine cartridge 120 is exhausted. As previously described, the medicine cartridge 120 is inserted into the cavity 116 (FIG. 1) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length. Optionally, some embodiments of the pump device 100 may include a label 117a that is adhered around the barrel 111. The label 117a may provide a convenient location for basic user instructions, product identification information, and other information related to the infusion pump system 10. To provide enhanced viewability of the medicine cartridge 120 through the label 117a, the label 117a may include a window 117b through which the user may visually inspect if the plunger 125 is nearing the end of its travel length.

As shown in FIG. 11, the pump device 100 has been used to a point at which the medicine cartridge 120 is exhausted. The plunger 125 has been advanced, toward the left in FIG. 11, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 (and through the window 117b of the label 117a in this embodiment) to determine if the medicine cartridge 120 is almost empty. When the user determines that a new medicine cartridge 120 should be employed, the pump device 100 can be readily separated from the controller device 200 by actuating the release member 215. In this embodiment, the release member 215 is a latch on the controller device 200 that is biased toward a locking position to engage the pump device 100. The latch 215 may be arranged to engage one or more features on a lateral side of the pump housing 110. As such, the user may actuate the release member 215 by moving the release member 215 in a lateral direction 216 (FIG. 11) away from the pump device 100 by applying a force with the user's finger).

As shown in FIG. 12, when the release member 215 is actuated and moved to a position away from the pump device 100, the segmented guide rail 114a-b is free to slide longitudinally in the guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 1) may be withdrawn from the mating depression 213 (FIG. 12), and the electrical connector 118 can be separated from the mating connector 218. In these circumstances, the pump device 100 is physically and electrically disconnected from the controller device 200 while the pump device retains the exhausted medicine cartridge 120.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., move in the lateral direction 216 in the embodiment shown in FIG. 11). Accordingly, in some embodiments, the pump device 100 can automatically and sharply move a small distance (e.g., about 0.5 mm to about 5 mm) away from the controller 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Figure 14:
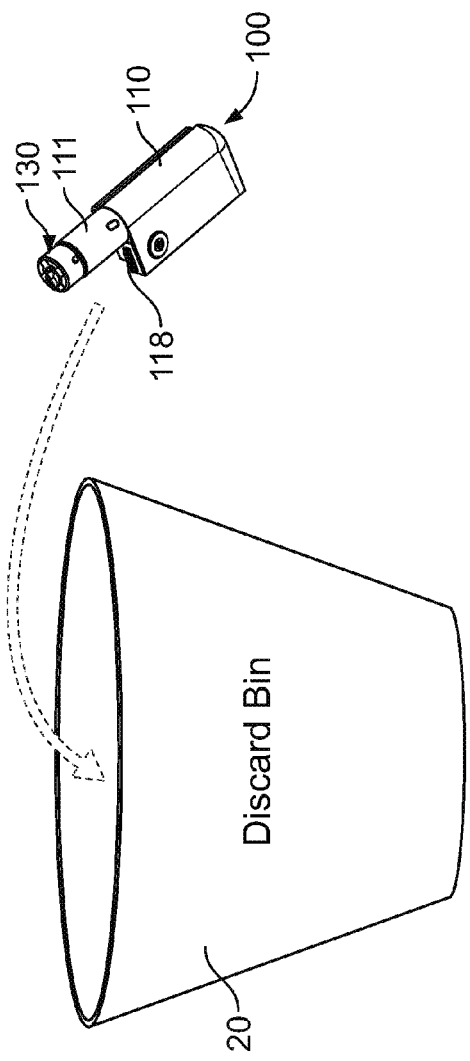

Referring to FIGS. 13-14, the same controller device 200 can be reused with a new pump device 100' having a new medicine cartridge 120' retained therein, and the previously used pump device 100 can be discarded with the exhausted medicine cartridge 120. The new pump device 100' (FIG. 13) can have a similar appearance, form factor, and operation as the previously used pump device 100 (FIGS. 11-12 and 14), and thus the new pump device 100' can be readily attached to the controller device 200 for controlled dispensation of medicine from the new medicine cartridge 120'. In some embodiments, the user may prepare the new pump device 100 for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 13, it should be understood that the tubing 147 may be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller 200) before attaching the infusion set patch to the user's skin. As shown in FIG. 13, the new medicine cartridge 120' may be filled with medicine such that the plunger 125 is not viewable through the barrel 111.

As shown in FIG. 14, the previously used pump device 100 that was separated from the controller device (as described in connection with FIGS. 11-12) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 20, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 146 (not shown in FIG. 14, refer to FIG. 8) that was used with the pump device 100 may be removed from the user and discarded into the bin 20 along with the pump device 100. Alternatively, the infusion set 146 can be disconnected from the previous pump device 100 and attached to the new pump device 100'. In these circumstances, the user may detach the infusion set cannula and patch from the skin so as to "re-prime" the tubing with medicine from the new pump device 100' to remove air pockets from the tubing. Thereafter, the infusion set cannula and patch can be again secured to the user's skin.

Referring to FIGS. 15-16, the new pump device 100' can be removably attached to the controller device 200 to assemble into the infusion pump system 10 for delivery of medicine to the user. Before the pump device 100 is electrically connected with the controller device 200, the user may prepare the new pump device 100' for use by pulling the removable tab 141 away from the pump housing 110. In this embodiment, the new pump device 100' includes the removable tab 141 to seal the battery in the unused pump device 100' and thereby maintain the battery in a storage mode (refer, for example, to FIG. 14 in which the removable tab 141 is arranged to cover an internal lace of a vent 145). The vent 145 can be implemented in some embodiments of the infusion pump system 10 having a power source arranged that draws upon surrounding air for optimum operation. Because the controller device 200 and the pump device 100 may be sealed to resist water migration during normal usage, the water-resistant vent instrument 145 may be used to provide the air to the power source without permitting migration of water therethrough. For example, in this embodiment, the pump device 100 may house a power source 345 in the form of a zinc-air cell battery (refer to FIG. 18), which draws upon the surrounding air during operation. When the pump device 100 is in use, the pump housing 110 is preferably sealed to protect the internal drive system and medicine cartridge from water migration. As such, the pump housing 110 may include the water-resistant vent 145 disposed proximate to the zinc-air cell battery 345 so that some air may pass through the vent 145 and toward the battery. The water-resistant vent instrument 145 may include one or more layers of a material that is permeable to air and resistant to passage of liquids such as water. For example, the water-resistant vent instrument 145 may include one or more layers of a GORE-TEX material to resist the migration of water into the pump device while permitting the passage of air toward the battery.

As described in more detail below, when the new pump device 100' is prepared for usage, the removable tab 141 can be pulled away from the pump housing 110 (and away from the battery therein), which switches the battery into an activation mode. Thus, the shelf-life of the pump device 100' (prior to usage with the controller device 200) may be extended by sealing the battery in a storage mode because little, if any, energy is dissipated from the battery when in the storage mode.

The new pump device 100' can be connected to the controller device 200 by advancing the new pump device 100' in a longitudinal direction 219 (FIG. 15) toward the controller device 200. When the pump device 100' is advanced in the longitudinal direction 219 toward the controller device 200, the movement is guided by the slider channel 112 (FIG. 8) and the segmented rails 114*a-b*. In particular, the slider channel 112 of the pump housing engages the rail 212 of the controller housing 210. Also, the front portion of the segmented rail 114*a* slides into the rear portion of the guide channel 214*b*. In this embodiment, the front portion of the segmented rail 114*a* includes a ramp surface 114*c* (refer also to FIG. 1) that engages a complementary ramp surface 215*c* (FIG. 8) of the release member 215 to thereby force the release member 215 away from the guide channel 214*a-b* during advancement of the pump device 100'. The release member 215 is temporarily forced away from the guide channel 214*a-b* so that the front portion of the segmented rail 114*a* passes over the release member 215, which enables the electrical connector 118 of the pump device 100' to engage with the mating connector 218 of the controller device 200. As the connectors 118 and 218 join together to form the electrical connection, the release member 215 is biased to return to its latched position and is shifted to a position in the guide channel 214a-b between the segmented rails 114a-b so as to prevent withdrawal of the pump device 100'.

As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction) that causes both a physical connection and an electrical connection. Thus, the infusion pump system 10 permits users to readily join the pump device 100' and the controller device 200 without compound or otherwise difficult hand movements—a feature that can be beneficial to child users or to elderly users.

As shown in FIG. 16, when the new pump device 100' is fully advanced and attached to the controller device 200, the gasket 140 is compressed between the opposing surfaces of the pump housing 110 and the controller housing 210. Such a configuration provides a water-resistance seal around the electrical connection that protects the sensitive internal components of the pump device 100' and the controller device 200 from damage or malfunction.

As previously described in connection with FIGS. 2-3, the tubing 147 of the infusion set 146 can be attached to the cap device 130 to provide a fluid path from the new pump device 100' to the user. Likewise, the external audio device 231 of the playback system 230 can be connected to the controller device 200 so as to deliver selected media content to the user.

In some embodiments, the playback system 230 can be configured to provide tutorial content or voice instructions to the user during the process previously described in connection with FIGS. 11-16. For example, when the user is going to detach the us controller device 200 and discard an exhausted pump device 100 (as previously described), the user can activate the playback system 230 to output voice instructions through the external audio device 231 that guides the user on the detachment operations. Furthermore, the voice instructions can guide the user through the operations of preparing a new pump device 100' and removably attaching the new pump device 100' to the controller device 200 in a manner that provides a secure fitting, an overall compact size, and a reliable electrical connection.

Referring now to FIG. 17, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100, in this embodiment, the control circuitry 240 includes a main processor board 242 that is in communication with a power supply board 244. The control circuitry 240 includes at least one processor 243 that coordinates the electrical communication to and from the controller device 200 (e.g., communication so between the controller device 200 and the pump device 100). The processor 243 can be arranged on the main processor board 242 along with a number of other electrical components such as at least one memory device 246. It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the memory device 246 arranged in the control circuitry 240. Furthermore, in some embodiments the memory device 246 can store executable software instructions for the processor 243. Alternatively, the control circuitry 240 may include other dedicated memory devices (e.g., separate from the memory device 246) that store executable software instructions for the processor 243. The control circuitry 240 may include other components, such as sensors, that are electrically connected to the main processor board 242. For example, at least a portion of an occlusion sensor system (not shown in FIG. 17) can be electrically connected to the main processor board 242 via a flexible circuit substrate or one or more wires.

As previously described, the controller device 200 can be electrically connected with the pump device 100 via mating connectors 118 and 218 (FIGS. 1 and 8) so that the control circuitry 240 can communicate control signals to the pump device 100 and receive feedback signals from components housed in the pump device 100. In this embodiment, the electrical connector 118 (FIG. 1) on the pump device 100 is a z-axis connector, and the connector 218 (FIG. 8) on the controller device 200 is adapted to mate therewith. The electrical connector 218 on the controller device 200 is in communication with the control circuitry 240. As such, the processor 243 can operate according to software instructions stored in the memory device 246 so as to send control signals to the pump device 100 via the connector 218.

The memory device 246 connected to the control circuitry 240 can be configured to store media content for use by the playback system 230. For example, the memory device 246 can electronically store a number of MP3 music files or other audio content data for subsequent playback to the user via the earbuds of external audio device 231. In some embodiments, the memory device 246 can include a first memory portion 247a that stores media content files, such as music, audiobooks, interactive games, images and other video data, or the like. The first memory portion 246a can be made available for updating or otherwise changing the media content files in accordance with the user's selections. In addition, the first memory portion 246a can include other information related to the media content stored therein, including title and artist/author information, playback history information, licensing and authorization information, playlist information, or the like.

The memory device 246 may also include a second memory portion 247b that is dedicated to storing infusion pump data, such as pump settings and menu options, basal and bolus dispensation data, executable software instructions (for the processor 243) that control the operation of the pump device 100, and the like. The second memory portion 247b can be selected to provide ample storage space for the infusion pump data so that the pump device 100 can safely dispense the medicine in accordance with the signals from the properly operating control device 200. In particular embodiments, the second memory portion 247b may be partitioned or segregated the first memory portion 247a or otherwise protected from overwriting during the process of updating or changing the media content files stored in the first memory portion 247a. In alternative embodiments, the memory device 246 may comprise a plurality of separate memory cards or memory chips accessible to the processor 243, some of which are dedicated to the media content data and others that are dedicated to the infusion pump data.

Still referring to FIG. 17, the playback system 230 can include an audio jack 232 or other media device output (e.g., wireless transmitter 231' for outputting media content data to the earpiece 235' shown in FIG. 5) that is electrically connected to the control circuitry 240. As such, the processor 243 can execute a media player software program stored in the memory device 246 so as to decode or otherwise retrieve one or more media content files and output signals via the audio jack 232. The signals output from the audio jack 232 can include audio signals that cause the external audio device 231 to generate audible sounds indicative of the selected media content (e.g., song, audiobook, voice instructions, or the like). In this embodiment, the audio jack 232 comprises a connector that mates with a plug end of the external audio device 231. The audio jack 232 can be arranged in the controller housing 210 so that it is generally aligned with the port 234 that receives the plug end of the external audio device 231.

Still referring to FIG. 17, the user interface 220 of the controller device 200 can include input components, output components, or both that are electrically connected to the control circuitry 240. For example, in this embodiment, the user interface 220 includes the display device 222 having an active area that outputs information to a user and four buttons 224a-d that receive input from the user. Here, the display 222 may be used to communicate a number of settings or menu options for the infusion pump system 10. In this embodiment, the control circuitry 240 may receive the input commands from the user's button selections and thereby cause the display device 222 to output a number of menus or program screens that show particular settings and data (e.g., review data that shows the medicine dispensing rate, the total amount of medicine dispensed in a given time period the amount of medicine scheduled to be dispensed at a particular time or date, the approximate amount of medicine remaining the cartridge 120, or the like). As previously described, the controller circuit 240 can be programmable in that the input commands from the button selections can cause the controller circuit 240 to change any one of a number of settings for the infusion pump system 10. In addition, the display 222 may be used to show the media content information 226 (FIG. 1) related to selected media content loaded by the playback system 230. Again, the control circuitry 240 may receive the input commands from the user's button selections and thereby cause the display device 222 to output a number of playlists, menus, or program screens that show media content settings and data (e.g., titles, artists, customized playlists, usage or playback statistics, or the like). As previously described, the controller circuit 240 can be programmable in that the input commands from the button selections can cause the controller circuit 240 to change any one of a number of media content settings.

As previously described in connection with FIGS. 7 and 8, some embodiments of the pump system 10 include a cable connector (e.g., a data cable port or a data cable that mates with connector 218) for communicating with a separate computer system. As such, the data cable may electrically connect to the control circuitry 240 to upload data or program settings to the controller circuit or to download data from the control circuitry 240. For example, historical data of medicine delivery can be downloaded from the control circuitry 240 (via the cable connector) to a computer system of a physician or a user for purposes of analysis and program adjustments. Optionally, the data cable may also provide recharging power.

Still referring to FIG. 17, the control circuitry 240 of the controller device 200 may include a second power source 245 that can receive electrical energy from a first power source 345 (FIG. 18) housed in the pump device 100. In this embodiment, the second power source 245 is coupled to the power supply board 244 of the control circuitry 240. The hand-wired transmission of the electrical energy can occur through the previously described connectors 118 and 218 (FIGS. 1 and 8). In such circumstances, the first power source 345 (FIG. 18) may include a high density battery that is capable of providing a relatively large amount of electrical energy for its package size, while the second power source 245 (FIG. 17) tray include a high current-output battery that is capable discharging a brief current burst to power the drive system 300 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, as previously described, the first battery 345 may comprise a zinc-air cell battery. The zinc-air cell battery 345 may have a large volumetric energy density compared to some other battery types. For example, the zinc-air cell battery 345 may have a volumetric energy density of greater than about 900 Watt-hours/Liter (Wh/L), about 1000 Wh/L to about 1700 Wh/L and about 1200 Wh/L to about 1600 Wh/L. Also, the zinc-air cell battery may have a long storage life, especially in those embodiments in which the battery is sealed (e.g., by the removable tab 141 or the like) during storage and before activation. One exemplary zinc-air cell battery provides a potential voltage of about 1.1V to about 1.6V (about 1.2V to about 1.4 V, and about 1.3 V in one embodiment), a current output of about 8 mA to about 12 mA (about 10 mA in one embodiment), and a storage capacity of greater than about 600 mA·h (about 650 mA·h in one embodiment).

As shown in FIG. 17, the second battery 245 may include a high current-output device that is housed inside the controller housing 210. The second battery 245 can be charged over a period of time by the first battery 345 and then intermittently deliver high-current bursts to the drive system 300 over a brief moment of time. In addition, the second battery 245 can be used to power the playback system 230 so that the selected media content (stored in the memory device 245) is delivered to the user (e.g., via the external audio device 231 in this embodiment). For example, the second battery 245 may comprise a lithium-polymer battery. The lithium polymer battery disposed in the controller device 200 may have an initial current output that is greater than the zinc-air cell battery disposed in the pump device 100, but zinc-air cell battery may have an enemy density that is greater than the lithium polymer battery (e.g., the lithium polymer battery disposed in the controller device 200 may have a volumetric energy density of less than about 600 Wh/L). In addition, the lithium-polymer battery 245 is readily rechargeable, which permits the zinc-air battery 345 disposed in the pump device 100 to provide electrical energy to the lithium-polymer battery 245 for purposes of recharging. One exemplary lithium-polymer battery provides a initial current output of about greater than 80 mA (about 90 mA to about 110 mA, and about 100 mA in one embodiment) and a maximum potential voltage of about 4.0V to and 4.4V (about 4.2 V in one embodiment). In other embodiments, it should be understood that the second power source 245 may comprise a capacitor device capable of being recharged over time and intermittently discharging a current burst to activate the drive system 300.

Accordingly, the infusion pump system 10 having two power sources 345 and 245—one arranged in the pump device 100 and another arranged in the reusable controller device 200—permits a user to continually operate the controller device 200 without having to recharge a battery via a wall-plug or other cable. Because the controller device 200 can be reusable with a number of pinup devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing (or possibly eliminating) the need for separate recharging of the controller device 200 via a power cord plugged into a wall outlet.

In particular embodiments, the activation of the media content playback system 230 may be limited if the controller device 200 detects that the remaining capacity of the power source (e.g., battery 245 in this embodiment) reaches below a threshold level. In such circumstances, the remaining battery power can be automatically reserved for use in operating the drive system 300 to deliver medicine to the user. Alternatively, the playback system 230 may be limited by the controller device 200 based on a power use profile. The power use profile can provide an estimate of remaining battery life based on the user's activity with the infusion pump system 10 (e.g., activations of the drive system to provide basal and bolus dispensations, historical interaction with the user interface 220, history of activating the playback system 230, and the like). Using this power use profile, the controller device 200 can estimate how long the remaining battery power will last in order to dispense the medicine remaining in the cartridge 120. If the power use profile indicates that the remaining battery power may be insufficient, particular features such as the playback system 230 may be limited or shut of in order to conserve the remaining battery power for activating drive system and indicating alarms. In another example, the controller device 200 may limit the number of uses of the playback system 230 to a predetermined amount of usage (e.g., total output time or the like) per day or per attachment of a new pump device 100. Again, providing a limit on the usage of playback system 230 can conserve the battery power for other operations such as alarm indications and the drive system.

Figure 18:
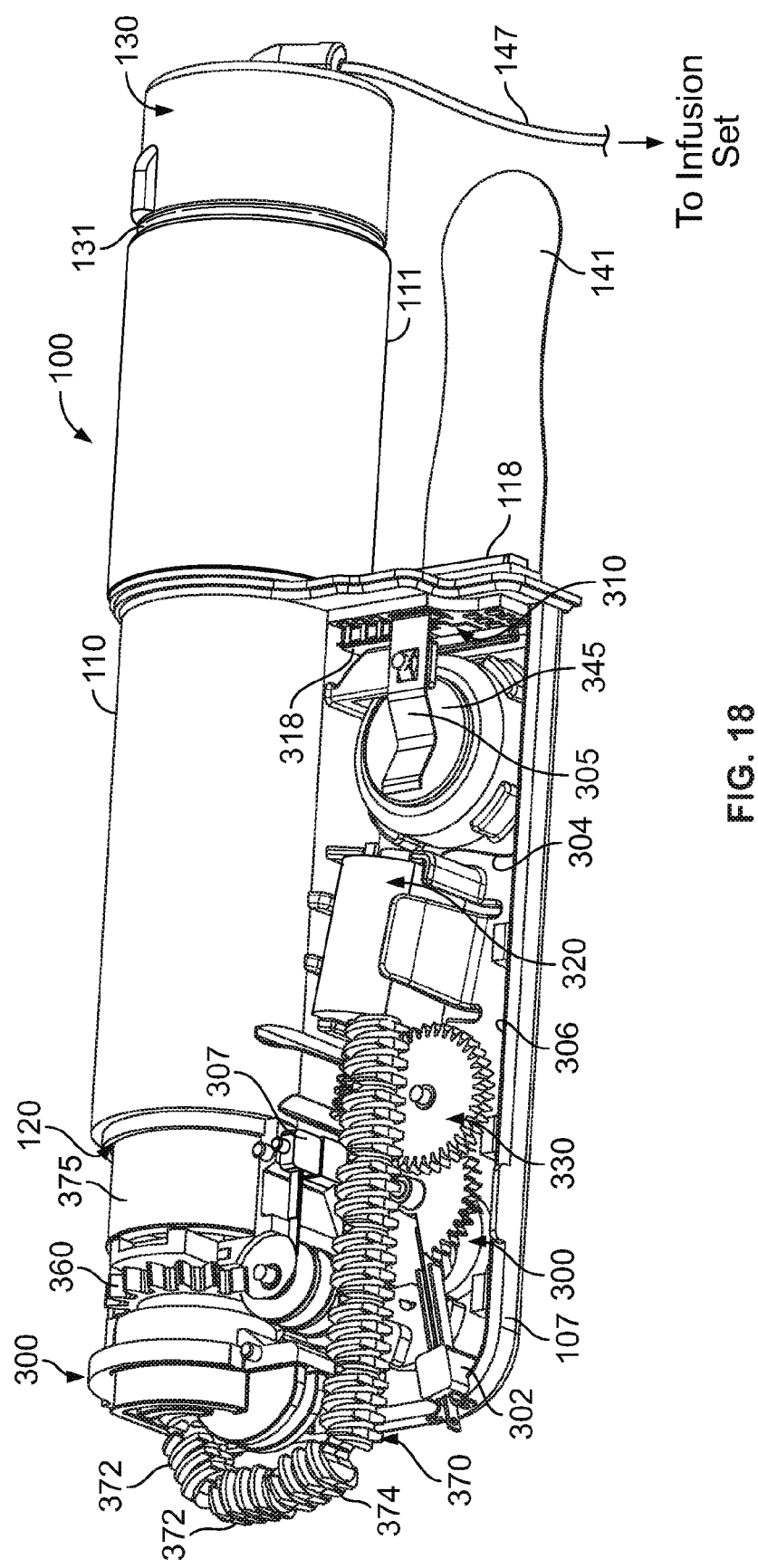
FIG. 18 is a perspective view of a pump device (with a housing portion removed) for an infusion pump system, in accordance with some embodiments.

Referring now to FIG. 18, the pump device 100 may include a drive system 300 that is controlled by the removable controller device 200 (FIGS. 1-3 and 8). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. In this embodiment, the pump housing 110 includes a chassis 107 that is at least partially covered by a shell portion (removed from FIG. 18 for purposes of illustrating the drive system 300). The shell portion can be used to cover at least a portion of the drive system 300. The shell portion can slide over and join with the chassis 107 (and other body portions) to form the assembled pump housing 110.

Some embodiments of the drive system 300 may include a battery powered actuator (e.g., reversible motor 320 or the like) that resets a ratchet mechanism 330, a spring device 350 (FIG. 22) that provides the driving force to the ratchet mechanism 330, and a drive wheel 360 that is rotated by the ratchet mechanism 330 to advance the flexible piston rod 370 toward the medicine cartridge 120. Also, the pump device 100 can include one or more motion detectors coupled with the drive system 300 to provide feedback regarding the operation of the drive system 300. For example, the pump device 100 may include a first motion detector 302 configured as a limit switch that detects when a portion of the ratchet mechanism 330 has reached the limit of its travel and must thereafter stop movement or reverse direction. In another example, the pump device 100 may include a second motion detector 307 in the form of a mechanical error switch that indicates whether components of the drive system 300 completed the desired motion for each drive cycle.

Still referring to FIG. 18, the pump device 100 includes a connector circuit 310 to facilitate the transfer of signals to and from the electrical connector 118 (FIG. 1). As previously described, the electrical connector 118 of the pump device 100 mates with the connector 218 (FIG. 8) of the controller device 200 so that electrical communication can occur between the pump device 100 and the controller device 200. The connector circuit 310 may comprise a generally non-complex circuit 310 that does not include a processor or other relatively high-cost components. In this embodiment, the connector circuit 310 operates as a passageway for the control signals (from the control circuitry 240 (FIG. 17) of the controller device 200) to transmit to the drive system 300 (e.g., to the actuator 320). For example, the reversible motor 320 may be connected to the connector circuit 310 via one or more wires 304. The connector circuit 310 also operates as a passageway for the electrical power from the first battery 345 (FIG. 18) to pass to the controller device 200 for recharging of the second battery 245 (FIG. 17). For example, the first battery 345 may be connected to the connector circuit 310 via one or more power contacts 305. Furthermore, the connector circuit 310 operates as a passageway for feedback signals (e.g., from the motion detectors 302 and 307) to transmit to the control circuitry 240 (FIG. 17) of the controller device 200. For example, the limit switch 302 may be connected to the connector circuit 310 via one or more wires 306 (the one or more wires connecting the mechanical error switch 307 to the connector circuit 310 are not shown in FIG. 18).

In some embodiments, the connector circuit 310 in the pump device 100 includes a memory device 318 that can store data regarding the pump device 100 and its operational history. For example, the memory device 318 of the connector circuit 310 may include a flash memory chip that is configured to store data such as: a unique serial number designated for the pump device 100, a manufacturer identifier code, and a drive cycle counter. The unique serial number designated for the pump device 100 and the manufacturer identifier code may be useful pieces of quality control information that remains with the pump device 100 throughout its shelf-life and operational life, if, for example, a manufacturing error is identified for a particular pump device 100, the unique serial number and the manufacturer identifier code (e.g., a lot code) can be used to promptly identify the manufacturing location and its manufacturing lot.

The drive cycle counter stored in the memory device 318 can be useful for maintaining an accurate estimate of the volume of medicine that remains in the medicine cartridge 120. For example, the number of drive cycles that are required to incrementally advance the plunger 125 and thereby dispense a full medicine cartridge 120 may be a predetermined value (e.g., in some embodiments, 6,300 drive cycles result in full dispensation of a new medicine cartridge). Accordingly, the drive cycle counter stored in the memory device 318 can keep track of the number of drive cycles that have occurred through the operational life of the pump device 100. Each time the motor 320 completes a new drive cycle and incrementally advances the piston rod 370 to dispense some medicine, the controller device 200 can store an updated value for the drive cycle counter stored in the memory device 318. When the updated value stored in drive cycle counter stored in the memory device 318 approaches the predetermined value, the controller device 200 can alert the user that the medicine cartridge is approaching exhaustion. Furthermore, because the memory device 318 is arranged in the pump device 100, the drive cycle counter stored in the memory device 318 remains local to the pump device 100. If the pump device 100 is temporarily disconnected from the controller device 200 and then reconnected (or reconnected to a different controller device 200), the controller device 200 can retrieve the value for the drive cycle counter stored in the memory device 318 and promptly ascertain how much medicine remains in the medicine cartridge 120.

Still referring to FIG. 18, in some embodiments, the flexible piston rod 370 comprises a plurality of segments 372 serially connected by hinge portions 373 so that the flexible piston rod 370 is adjustable from a curved shape to a non-curved shape. The plurality of segments 372 and the interconnecting hinge portions 373 can be integrally formed in one piece from one or more moldable materials, including polymer materials such as Nylon or POM. In this embodiment, each of the plurality of rod segments 372 includes an exterior thread pattern 374 along at least one cylindrical surface portion. The piston rod 370 also includes a plunger engagement device 375 can be arranged at a forward end of the piston rod 370. As such, the plunger engagement device 375 faces toward the medicine cartridge 120 when the medicine cartridge 120 is inserted into the cavity 116. In some embodiments, the plunger engagement device 375 may comprise a pusher disc that abuts against the plunger 125 of the medicine cartridge 120.

Because the flexible piston rod 370 is adjustable from a curved shape to a noncurved shape, the overall length of the pump device can be reduced in some embodiments. For example, in a typical infusion pump that houses a straight and rigid rod, the typical infusion pump requires a package or housing having a linear dimension sufficient to accommodate the length of the rigid piston rod when it is at its limit of travel in which it is fully withdrawn from the container or cylinder. The pump device 100 incorporating the flexible piston rod 370 can require less space than a similar device that houses a non-flexible, rigid rod.

Figure 19:
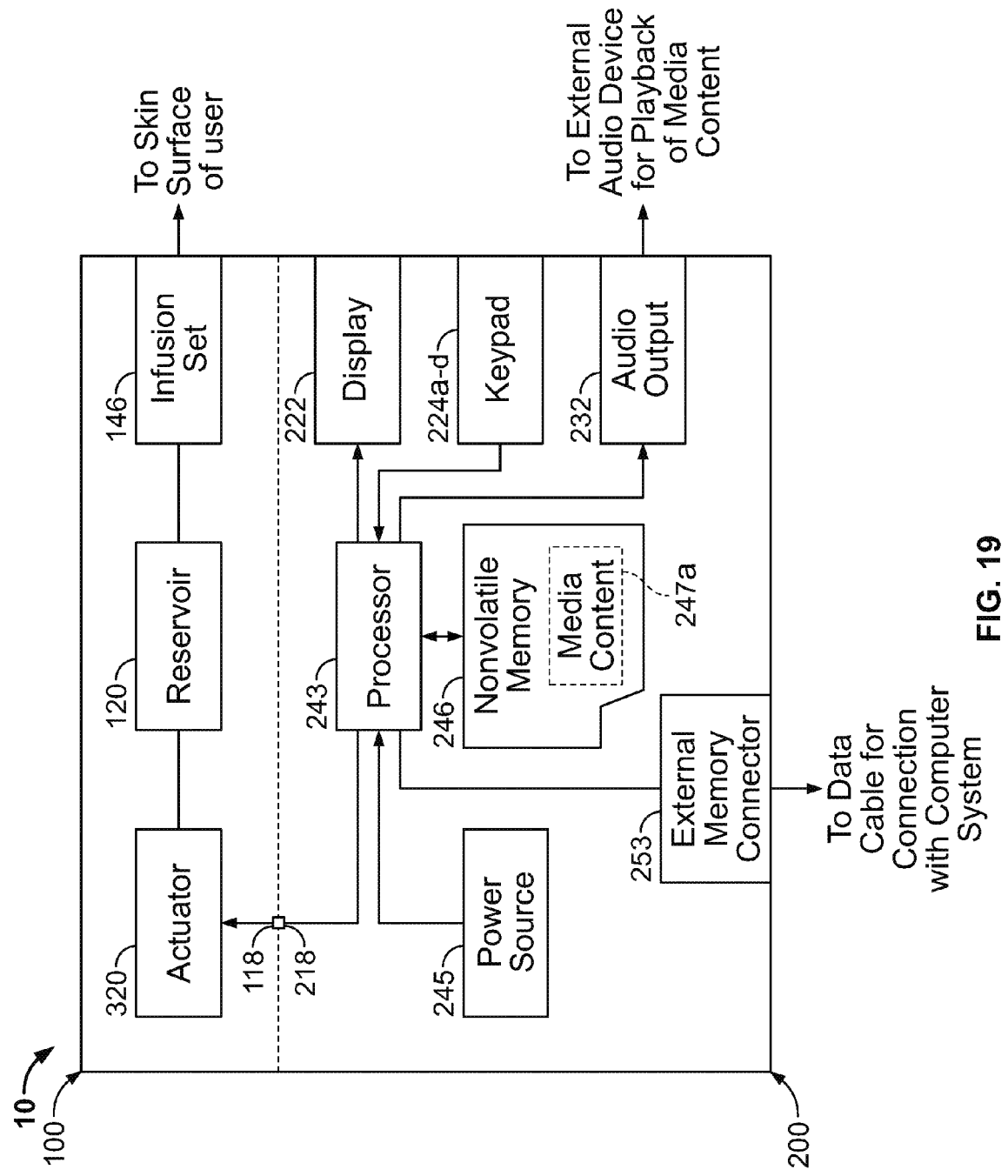
FIG. 19 is a diagram of an infusion pump system configured to deliver medicine to a user and to deliver media content to a user, in accordance with some embodiments.

Referring now to FIG. 19, a block diagram of the pump system 10 illustrates the operation of some components of the pump device 100 and the controller device 200. The controller device 200 is removably attached to the pump device 100 so as to form an electrical connection between connectors 118 and 218 (previously described in FIGS. 1 and 8). The controller device 200 includes the previously described processor 243, memory device 246, power source 245, display 222, and keypad buttons 224*a-d*. Such components can be used to control the activation of the pump device 100 so as to dispense a medicine dosage to the user. For example, the processor 243 can execute pump operation instructions stored in the memory 244 in accordance with the pump settings (some of which can be adjusted by the user with the display 222 and keypad buttons 224*a-d*). As such, the processor 243 can cause an activation signal to be sent from the controller device 200 to the actuator 320 in the pump device 100. As previously described, the activation power for the actuator 320 can be provided from the power source 245 located in the controller device 200.

In addition, the pump system 10 is a capable of providing media content playback while worn by the user and while dispensing medicine to the user. As shown in FIG. 19, this embodiment of the pump system includes the audio output 232, which can be an audio jack for connection with an external audio device 231 (FIG. 4) or a wireless transmitter for communication with the audio earpiece 235' (FIG. 5). Also, the memory 246 housed in the controller device 200 can store a number of media content files. As previously described, the memory 246 can include a selected portion 247*a* that is reserved for the storage of media content files. In addition, some embodiments of the pump system 10 include an external memory connector. In this embodiment, the external memory connector comprises the cable connector 253 for connection via the data cable 252 to a separate computer system, as previously described in connection with FIG. 7. Alternatively, the external memory connector may comprise the memory card port 251 for connection to with the removable memory card 250, as previously described in connection with FIG. 6. Accordingly, the pump system 10 can be configured to permit the user to update or otherwise change the media content files that are stored in the memory 246.

Figure 20A:
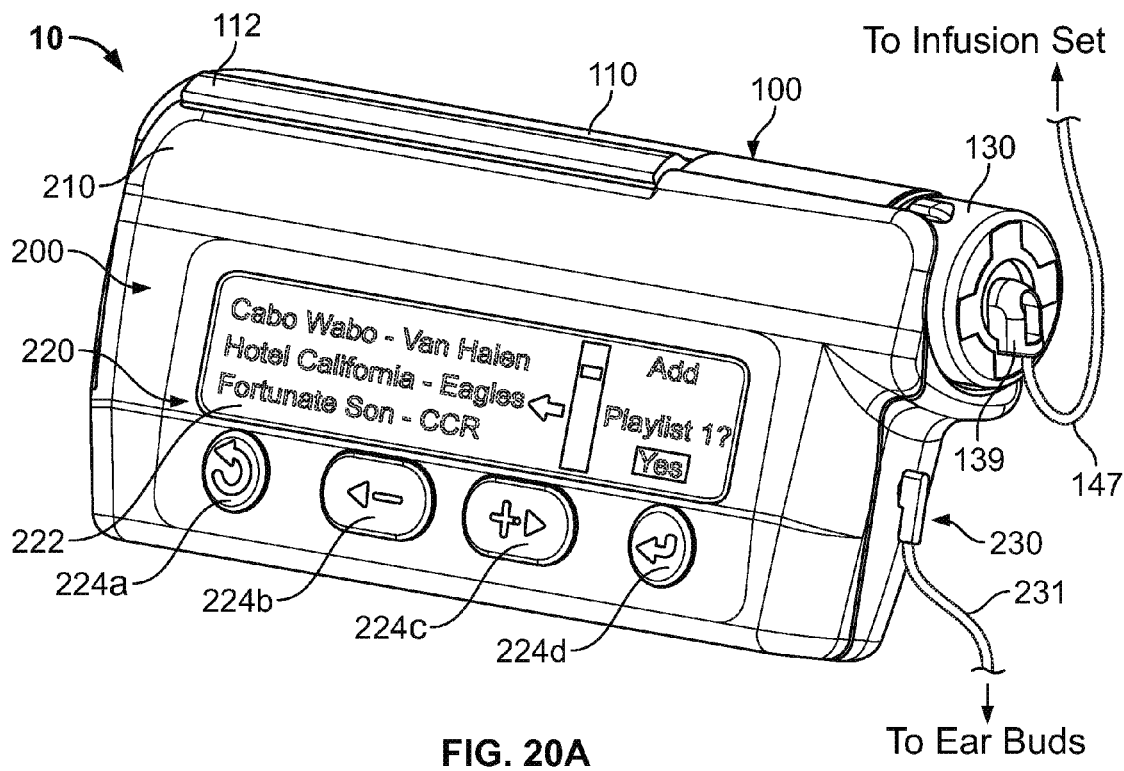
FIGS. 20A-B are perspective views of the infusion pump system displaying a collection of media content for playback to a user, in accordance with some embodiments.
Figure 20B:
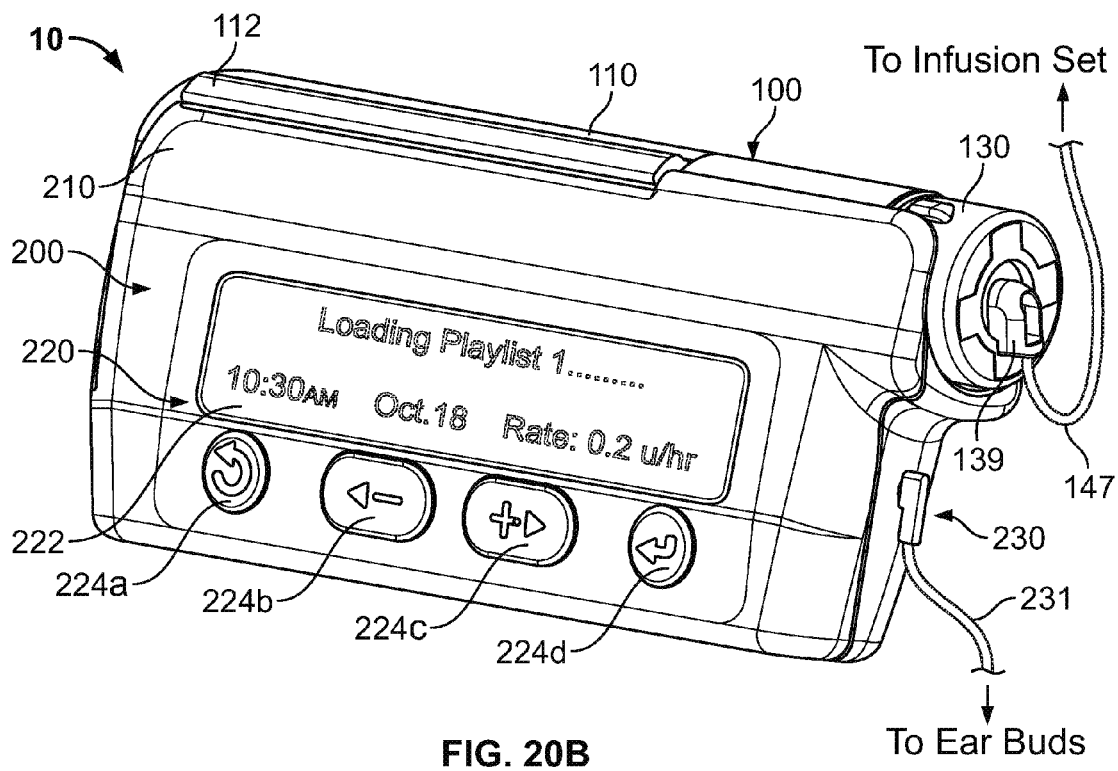

Referring now to FIGS. 20A-B, the pump system 10 can be configured to group a number of media content files into one or more playlists. In particular, the user can customize and save a playlist so that the playback system 230 will thereafter deliver the selected group of media content files when the playlist is activated. As previously described, the user interface 220 of the pump system 10 can include display numerals, text, symbols, images, or a combination thereof in order to communicate media content information to the user. For example, the display device 222 can be used to communicate a menu option in which the user can select particular media content file for assignment to a customized playlist. As shown in FIG. 20A, the display device 222 can display a list of media content files (e.g., MP3 music files in this embodiment) that are stored on the memory device 246 (FIG. 17). In this embodiment, the user may press the buttons 224*b* and 224*c* to scroll through list of media content files. When the user encounters a song the that should added to the particular playlist (e.g., "Playlist 1" in this embodiment), the user can actuate the button 224*d* positioned adjacent to the "YES" indicator in the display 222. A similar process can be used to remove selected media content files from a previously saved playlist.

As shown in FIG. 20B, the user can press one or more of the buttons 224*a-d* to select menu options for the playback system 230, including an option to playback a particular playlist (e.g., "Playlist 1" in this embodiment). As previously described, when the use activates the playback system 230, the processor 243 can execute a media player software program stored in the memory device 246 so as to decode or otherwise retrieve one or more media content files and output signals via the audio jack 232 (refer to FIG. 17). The signals output from the audio jack 232 can include audio signals that cause the external audio device 231 to generate audible sounds indicative of the particular media content organized in the selected playlist. In this embodiment, the display device 222 may include a media content message (e.g., "Loading Playlist 1 . . . " as shown, for example, in FIG. 20B) that indicates to the user that the media player has been activated to output the media content.

Figure 21A:
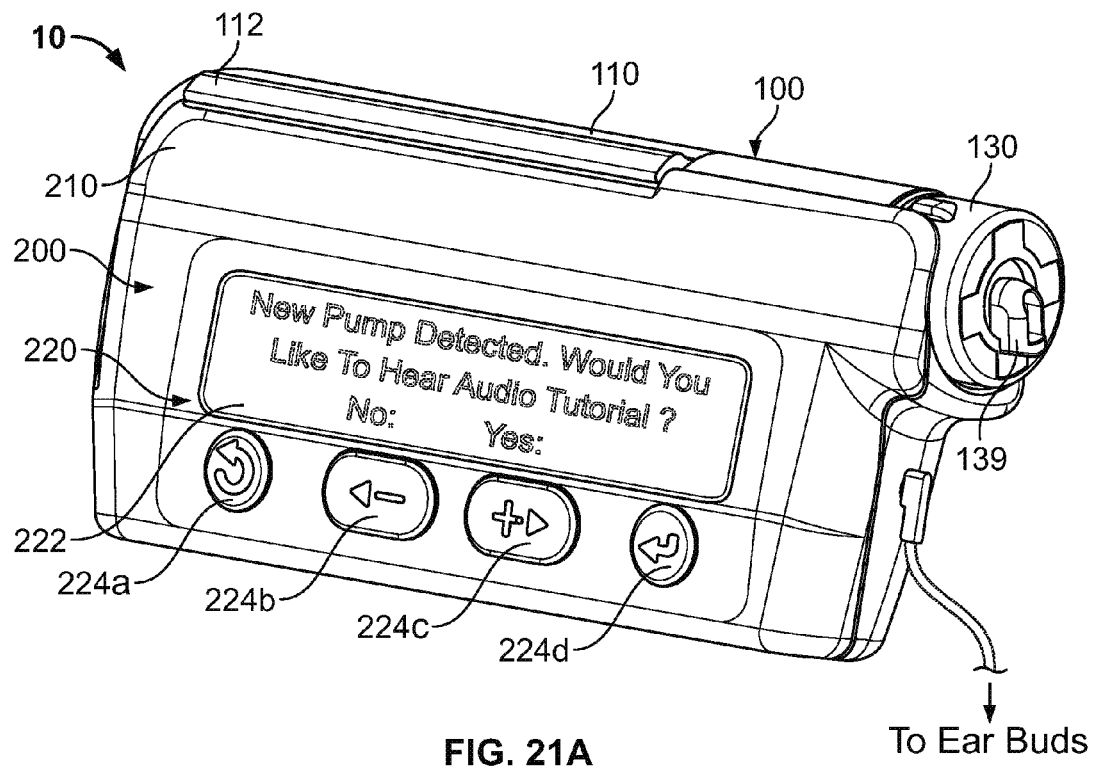
FIGS. 21A-B are perspective views of the infusion pump system prompting a user to receive instructional media content, in accordance with some embodiments.
Figure 21B:
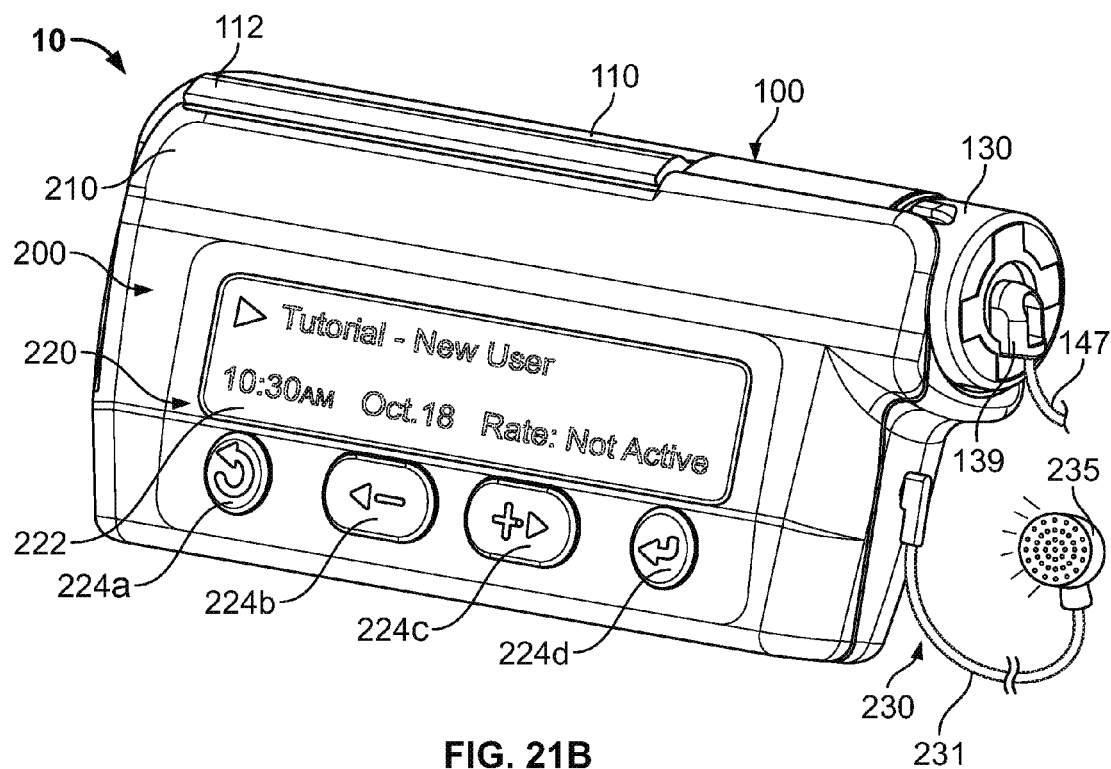

Referring now to FIGS. 21A-B, the media content stored in the memory 246 of the pump system 10 can include an instructional content that provides a tutorial on how to operate particular features of the system 10. Such media content can be used to provide training to new users (especially for children or other users that may require additional training outside of a clinic). In this example, the instructional content can include an audio tutorial on how to prepare the pump system 10 for medicine dispensation after a new pump device 100 can be connected to the controller device 200. As previously described in connection with FIGS. 11-16, the controller device can be reused with a new pump device 100' after a previously used pump device is emptied, expired, or otherwise exhausted. In such embodiments, the controller device 200 can detect when the new pump device 100 is connected thereto, and the display device 222 can be used to query whether the user would like to receive the audio tutorial. As shown in FIG. 21A, the display device 222 can prompt the user to indicate whether the audio tutorial or other instructional content) should be delivered through the playback system 230. The user can actuate the button 224b (adjacent to the "No" indicator) to input that no audio tutorial should be played at this time. Alternatively, the user can actuate the button 224c (adjacent to the "Yes" indicator) to input that the audio tutorial should be started. In some embodiments, the controller device 200 can be configured to automatically display the query screen 222 (as illustrated in FIG. 21A) for a limited period of time. For example, the query screen 222 (as illustrated in FIG. 21A) may be automatically displayed in response to the attachment of a new pump device only for a period of one month after the controller device 200 is initially activated. Accordingly, as the user becomes accustom to the operation of the pump system 10 over the period of the initial mouth, the user may no longer need to receive the playback of the audio tutorial for this particular feature.

As shown in FIG. 21B, when the user indicates that the audio tutorial should be played, the processor 243 can execute a media player software program stored in the memory device 246 so as to decode or otherwise retrieve the selected file containing the instructional content and output signals via the audio jack 232 (refer to FIG. 17). The signals output from the audio jack 232 can include audio signals that cause the external audio device 231 to generate voice instructions indicative of the selected tutorial. For example, the audio tutorial may provide voice instructions from the earbuds 235 that explain to the user how to attach the infusion set tubing 147 (compare FIG. 21A to FIG. 21B) or how to prime the infusion set tubing that was previously attached. The media content stored in the memory 246 of the pump system 10 may include other audio tutorials that provide instructions related to, for example, inserting the infusion set into the skin site, setting a new basal rate, setting a time-based basal rate program, activating a bolus dose, calculating a bolus dose based upon food intake, downloading software updates for the controller device 200, uploading historical dispensation data for review by a physician, periodically inspecting the pump system 10, and other actions to be performed by the user.

Figure 22:
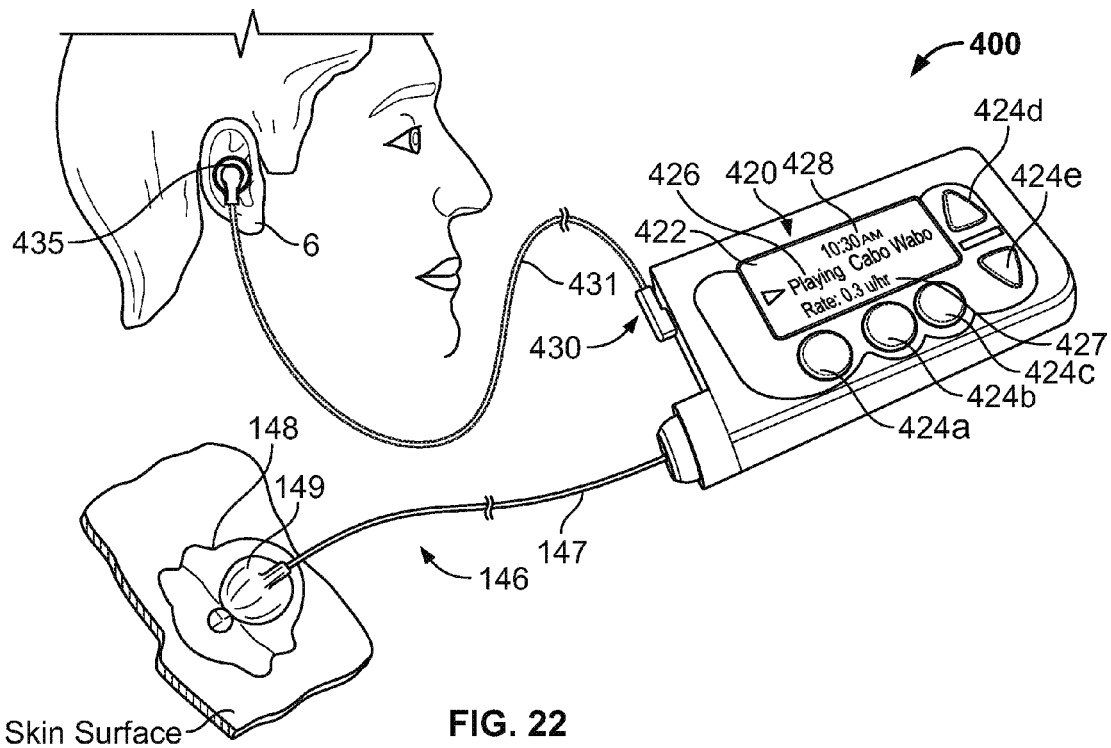
FIG. 22 is a perspective view of another pump system configured to deliver medicine to a user and to deliver media content to a user, in accordance with certain embodiments.
Figure 23:
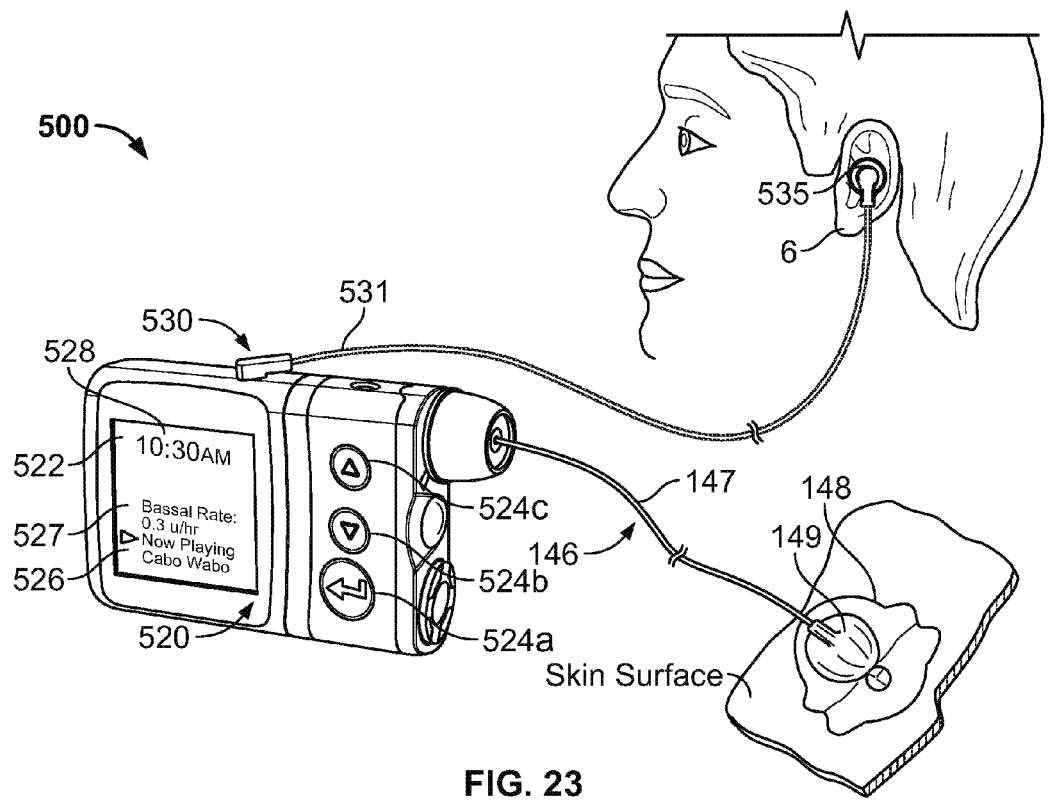
FIG. 23 is a perspective view of an alternative pump system configured to deliver medicine to a user and to deliver media content to a user, in accordance with some embodiments.
Figure 24:
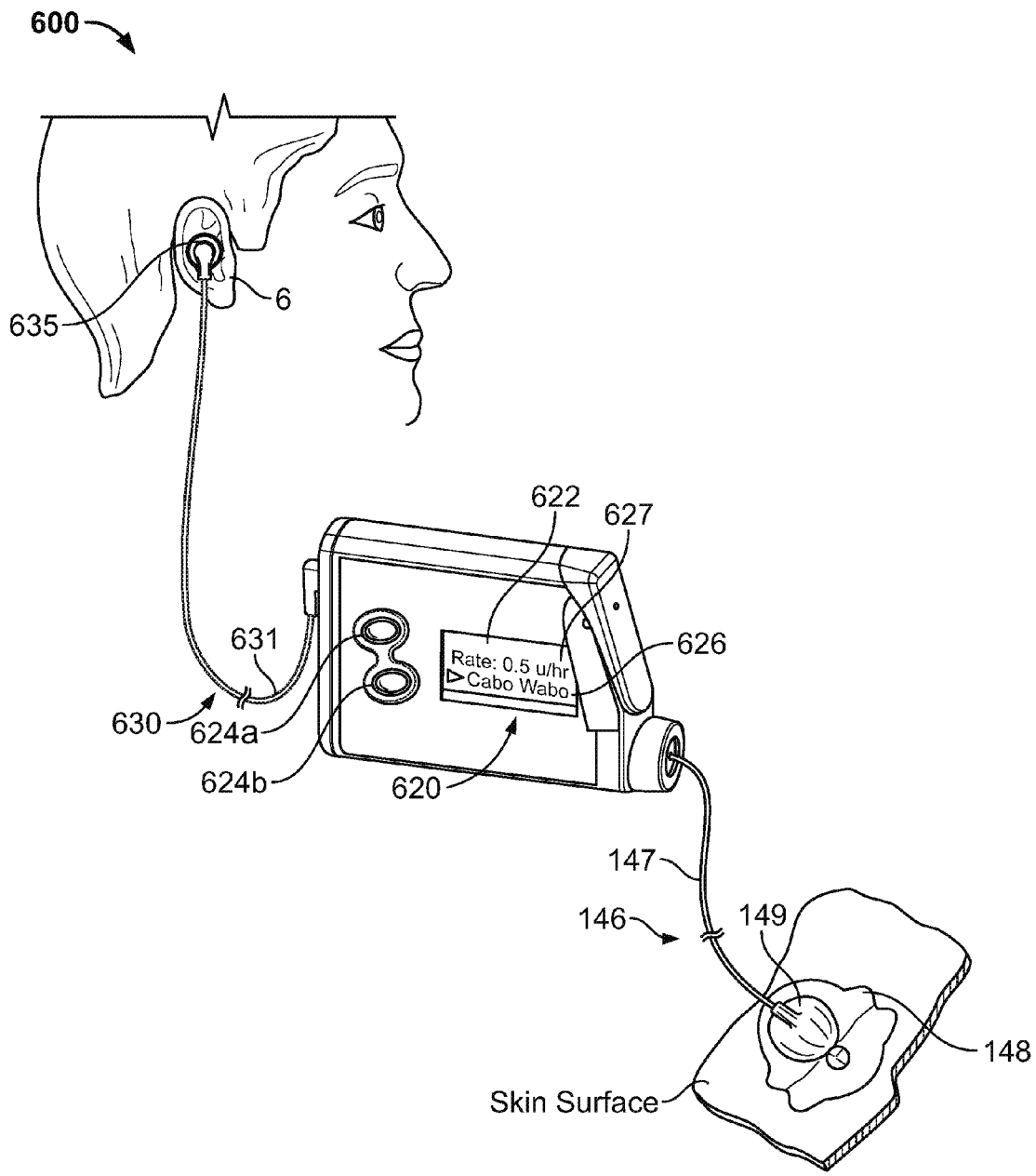
FIG. 24 is a perspective view of yet another pump system configured to deliver medicine to a user and to deliver media content to a user, in accordance with particular embodiments.

Referring now to FIGS. 22-24, some embodiments of a portable infusion pump system 400, 500, and 600 having media player capabilities can employ a reusable pump apparatus (rather than a disposable pump device as previously described). In such circumstances, the infusion pump system 400, 500, and 600 may comprise a reusable device that houses the control circuitry and the pump drive system. Similar to previously described embodiments, the infusion pump system 400, 500, and 600 may also include an media content playback system 430, 530, and 630 that can playback media content to the user contemporaneously with the dispensation of medicine to the user. Accordingly, the user can operate the reusable pump device so as to receive controlled, delivery of a medicine while also listening to the playback of selected MP3 music or other media content. As previously described, the pump system 400, 500, and 600 having the media content playback system 430, 530, and 630 may provide a compact, multi-purpose device that eliminates the need for the user to carry multiple devices (e.g., a medical pump device and a separate media player device). Also, the infusion pump system 400, 500, and 600 can enhance user safety by interrupting the music content or other media content in order to deliver an alarm to the user that might otherwise go unnoticed if the user was listening to a separate media player device.

In the particular embodiment depicted in FIG. 22, the pump system 400 comprises a reusable pump device that houses both the controller circuitry and the pump drive system. Similar to previously described embodiments, the pump system 400 can include a housing structure that defines a cavity in which a medicine cartridge can be received (not shown in FIG. 22; refer for example to cartridge 120 in FIG. 1). For example, the pump system 400 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. In this embodiment, the user can wear the portable pump system 400 on the user's skin under clothing or in the user's pocket while receiving the medicine dispensed through the infusion set 146.

Still referring to FIG. 22, the infusion pump system 400 may also include a media content playback system 430 that can playback media content (e.g., music, voice instructions, audiobooks, audio that corresponds to a video being displayed, and other data) to the user while the pump system 400 is delivering the medicine to the user. Similar to previously described embodiments, the playback system 430 may comprise an external audio device 431 that plugs into a connection port along the pump housing so as to mate with an audio output device (e.g., an audio jack similar to the component 232 shown in FIG. 17). The external audio device 431 may include earbuds 435 or another listening device that deliver sound to the user's ear while the pump system 400 is carried by the user. At least one memory device arranged in the pump system 400 can be used to electronically store a number of media content files available for playback to the user. Accordingly, the user can operate a user interface 420 of the infusion pump system 400 so as to receive controlled delivery of a medicine while also listening to the playback of selected MP3 music or other media content.

In this embodiment, the user interface 420 includes a display device 422 and one or more user-selectable buttons 424a-e. The display device 422 can include an active area in which numerals, text, symbols, images, or a combination thereof can be displayed (as shown, for example, in FIG. 22). For example, the display device 422 can be used to communicate media content information 426, which may related to the selected media content that is being delivered to the user through the playback system 430. Also, the display device 422 can be used to communicate a number of settings or menu options for the infusion pump system 400. For example, the display device 422 can be used to communicate medicinal delivery information 427, such as the basal delivery rate (as shown in FIG. 22), a bolus dosage, a historical record of medicine delivered, the amount of medicine remaining in the cartridge, or the like. In another example, the display device 422 can be used to communicate time and date information 428, which can be used by the user to determine dosage schedules, bolus delivery times, meal times, or the like.

Accordingly, the user may press one or more of the buttons 424a, 424b, 424c, 424d, and 424e to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). Also, the user can adjust the settings or otherwise program the pump system 400 by pressing one or more buttons 424a, 424b, 424c, 424d, and 424e of the user interface 420. Furthermore, the user can press one or more of the buttons 424a, 424b, 424c, 424d, and 424e so as to play, pause, rewind, or fast-forward the selected media content 426 or to otherwise control the output of media content through the playback system 430. Thus, the user can contemporaneously monitor the operation of the pump system 400 and control the media content playback from the saute user interface 420. Similar to previously described embodiments, the pump system 400 can be configured to interrupt the music content or other media content in order to deliver an alarm via the user's external audio device 431 (e.g., earbud device, other headphone device, or the like), thereby enhancing the user safety. Finally, the media content played by the pump system 400 may include an audio tutorial or other instructional content on how to operate particular features of the system, which facilitates new user training.

Referring now to the particular embodiment depicted in FIG. 23, the pump system 500 comprises a reusable pump device that houses both the controller circuitry and the pump drive system. Similar to previously described embodiments, the pump system 500 can include a housing structure that defines a cavity in which a medicine cartridge can be received. For example, the pump system 500 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. Again, the user can wear the portable pump system 500 on the user's skin under clothing or in the user's pocket while receiving the medicine dispensed through the infusion set 146.

The infusion pump system 500 may also include a media content playback system 530 that can playback media content to the user while the pump system 500 is delivering the medicine to the user. Similar to previously described embodiments, the playback system 530 may comprise an external audio device 531 that plugs into a connection port along the pump housing so as to mate with an audio output device (e.g., an audio jack or the like). The external audio device 531 may include earbuds 535 or another listening so device that deliver sound to the user's ear while the pump system 500 is carried by the user. At least one memory device arranged in the pump system 500 can be used to electronically store a timber of media content files available for playback to the user. Accordingly, the user can operate a user interface 520 of the infusion pump system 500 so as to receive controlled delivery of a medicine while also listening to the playback of selected MP3 music or other media content.

Still referring to FIG. 23, the user interface 520 includes a display device 522 and one or more user-selectable buttons 524a-c. The display device 522 can include an active area in which numerals, text, symbols, images, or a combination thereof can be displayed. For example, the display device 522 can be used to communicate media content information 526, which may related to the selected media content that is being delivered to the user through the playback system 530. Also, the display device 522 can be used to communicate a number of settings or menu options for the infusion pump system 500. For example, the display device 522 can be used to communicate medicinal delivery information 527, such as the basal delivery rate (as shown in FIG. 23) or the like. In another example, the display device 522 can be used to communicate time and date information 528. Similar to previously described embodiments, the user may press one or more of the buttons 524a, 524b, and 524c to shuffle through a number of menus or program screens that show particular settings and data related to the medicine dispensation. Also, the user can adjust the settings or otherwise program the pump system 500 by pressing one or more buttons 524a, 524b, and 524c of the user interface 520. Furthermore, the user can press one or more of the buttons 524a, 524b, and 524c so as to play, pause, rewind, or fast-forward the selected media content 526 or in otherwise control the output of media content through the playback system 530. Accordingly, the user can contemporaneously monitor the operation of the pump system 500 and control the media content playback from the same user interface 520. Similar to previously described embodiments, the pump system 500 can be configured to interrupt the music content or other media content in order to deliver an alarm via the user's external audio device 531, thereby enhancing the user safety. Also, the media content played by the pump system 500 may include an audio tutorial or other instructional content on how to operate particular features of the system, which facilitates new user training.

Referring now to FIG. 24, the pump system 600 comprises a reusable pump device that houses both the controller circuitry and the pump drive system. Similar to previously described embodiments, the pump system 600 can include a housing structure that defines a cavity in which a medicine cartridge can be received. For example, the pump system 600 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. The user can wear the portable pump system 600 on the user's skin under clothing or in the user's pocket while receiving the medicine dispensed through the infusion set 146.

The infusion pump system 600 in this embodiment also includes a media content playback system 630 that can playback media content to the user while the pump system 600 is delivering the medicine to the user. Similar to previously described embodiments, the playback system 630 may comprise an external audio device 63 that plugs into a connection port along the pump housing so as to mate with an audio output device (e.g., an audio jack or the like). The external audio device 531 may include earbuds 635 or another listening device that deliver sound to the user's ear while the pump system 600 is carried by the user. At least one memory device arranged in the pump system 600 can be used to electronically store a number of media content files available for playback to the user. Accordingly, the user can operate a user interface 620 of the infusion pump system 600 so as to receive controlled delivery of a medicine while also listening to the playback of selected MP3 music or other media content.

Still referring to FIG. 24, the user interface 620 includes a display device 622 and one or more user-selectable buttons 624a and 624b. The display device 622 can include an active area in which numerals, text, symbols, images, or a combination thereof can be displayed. For example, the display device 622 can be used to communicate media content information 626, which may related to the selected media content that is being delivered to the user through the playback system 630. Also, the display device 622 can be used to communicate medicinal delivery information 627, such as the basal delivery rate (as shown in FIG. 24) or the like. Similar to previously described embodiments, the user may press one or more of the buttons 624a and 624b to shuffle through a number of menus or program screens that show particular settings and data related to the medicine dispensation. Also, the user can adjust the settings or otherwise program the pump system 600 by pressing one or more buttons 624a and 624b of the user interface 620. In another example, the user can press one or more of the buttons 624a and 624b so as to play, pause, rewind, or fast-forward the selected media content 626 or to otherwise control the output of media content through the playback system 630. Accordingly, the user can contemporaneously monitor the operation of the pump system 600 and control the media content playback from the same user interface 620. Similar to previously described embodiments, the pump system 600 can be configured to interrupt the music content or other media content in order to deliver an alarm via the user's external audio device 631, thereby enhancing the user safety. Also, the media content played by the pump system 600 may include an audio tutorial or other instructional content on how to operate particular features of the system, which facilitates new user training.

Figure 25:
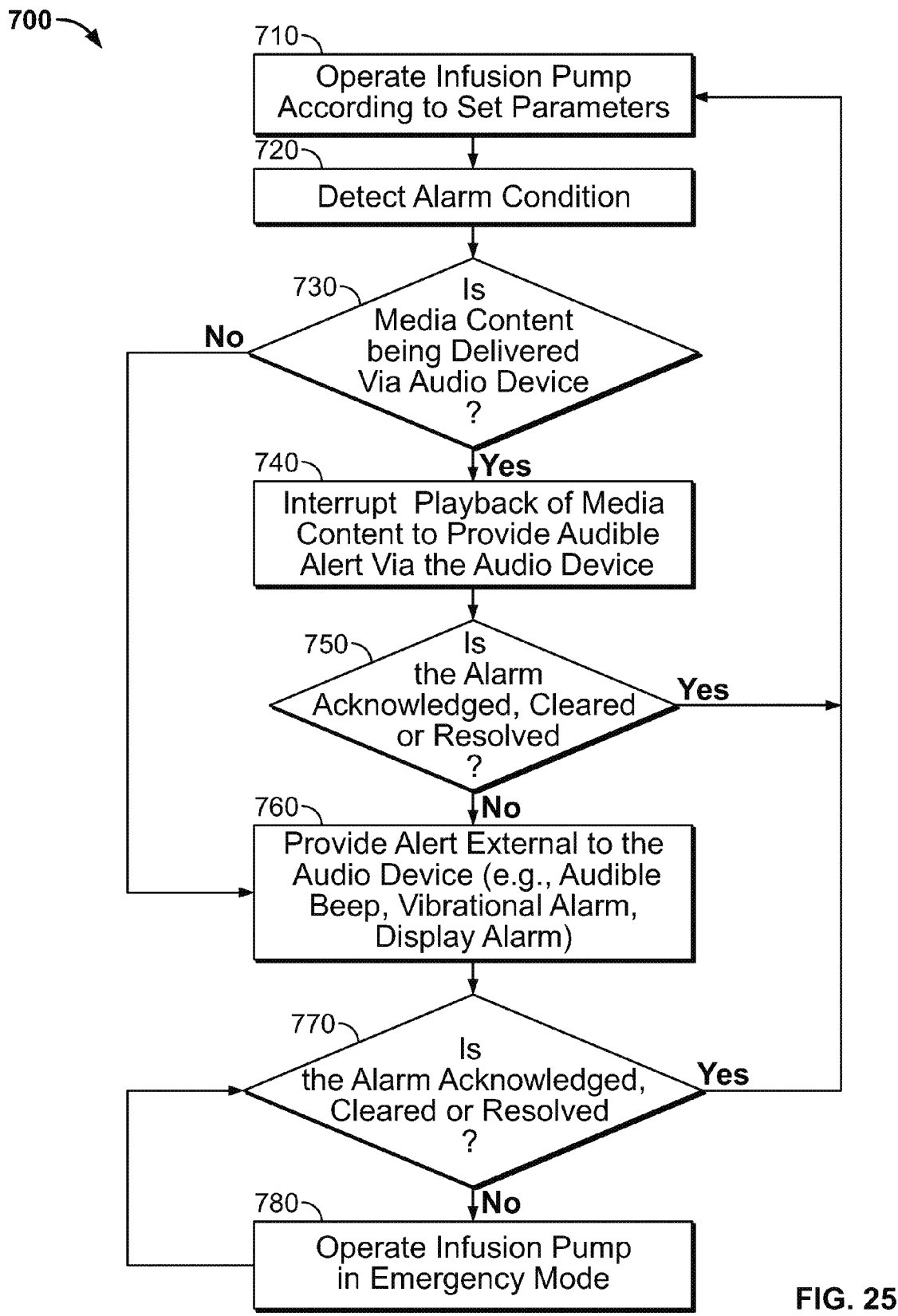
FIG. 25 is a chart describing a process for delivering an alert to a user of an infusion pump system, in accordance with some embodiments.

Referring now to FIG. 25, the infusion pump system 10 depicted in FIGS. 1-3 can be configured to interrupt the playback of media content when an alarm condition has been detected. As such, the pump system 10 can execute a process 700 that communicates the alum condition to the user. It should be understood from the description herein that the system 400, 500, and 600 can also be configured to operate as described in FIG. 25 so as to interrupt the playback of media content when an alarm condition has been detected.

The process 700 includes the operation 710 of operating the infusion pump according to the set parameters. For example, during normal usage, the pump device can dispense the medicine to the user in a controlled manner according to a selected basal rate. In operation 720, an alarm condition is detected by the infusion pump system. As previously described, the alarm condition may comprise an occlusion in the infusion set tubing 147, low battery power, low medicine remaining in the cartridge, a missed bolus dosage, or the like.

As shown in FIG. 25, the infusion pump system 10 can perform operation 730 so as to determine whether media content is being delivered to the user via an audio device. For example, the control circuitry can be equipped to detect whether the external audio device 231 is plugged into the audio jack 232 (refer to FIG. 17). In addition or in the alternative, the control circuitry can be used to determine whether the media content playback software has been activate to deliver media content to the user. If the operation 730 reveals that the media content is being delivered to the user, the process 700 proceeds to operation 740 in which the playback is interrupted to provide an audible alert via the audio device (e.g., a beep or voice warning is communicated via the earbuds 235 or the like). Alternatively, if the operation 730 reveals that no media content is being delivered, the pump system 10 proceeds to operation 760 in which an alert. (e.g., an audible beep, a vibration alarm, a display alarm, or the like) external to the audio device is provided to the user.

Referring again to operation 740, after the playback of the media content has been interrupted to provide the alert, the process 700 proceeds to operation 750 in order to determine if the alarm has been acknowledged, cleared, or otherwise resolved by the user. For example, as previously described in connection with FIG. 3, the user can actuate a button on the user interface 220 to acknowledge that the alarm was received. If the alarm is acknowledge or otherwise resolved, the process 700 cycles back to operation 710 where the pump system 10 functions according to the set parameters. If the alarm is not acknowledge or otherwise resolved, the process 700 can proceed to previously described operation 760 in which an alert (e.g., an audible beep, a vibration alarm, a display alarm, or the like) external to the audio device is provided to the user.

If the process reaches operation 760 to provide the alert external to the audio device, the process then determines in operation 770 if the alarm was acknowledged, cleared, or otherwise resolved by the user. If yes, the process 700 cycles back to operation 710 where the pump system 10 functions according to the set parameters. However, if the alarm has not been acknowledged or otherwise resolved, the process 700 proceeds to operation 780 in which the pump system 10 begins to operate in an emergency mode. The emergency mode can include a number of different operations depending upon the alarm condition that was detected. For example, the emergency mode may comprise a series of incrementally louder alarms that are intended to be heard from a distance away from the pump system (e.g., to get attention from others near the user). In another example, the emergency mode may comprise a shutdown of non-medical features so as to preserve the remaining battery power for medicine dispensation purposes. If the alarm condition is subsequently resolved, the user may operate the user interface 220 so as to return the pump system 10 to normal operation according to the set parameters.

Figure 26:
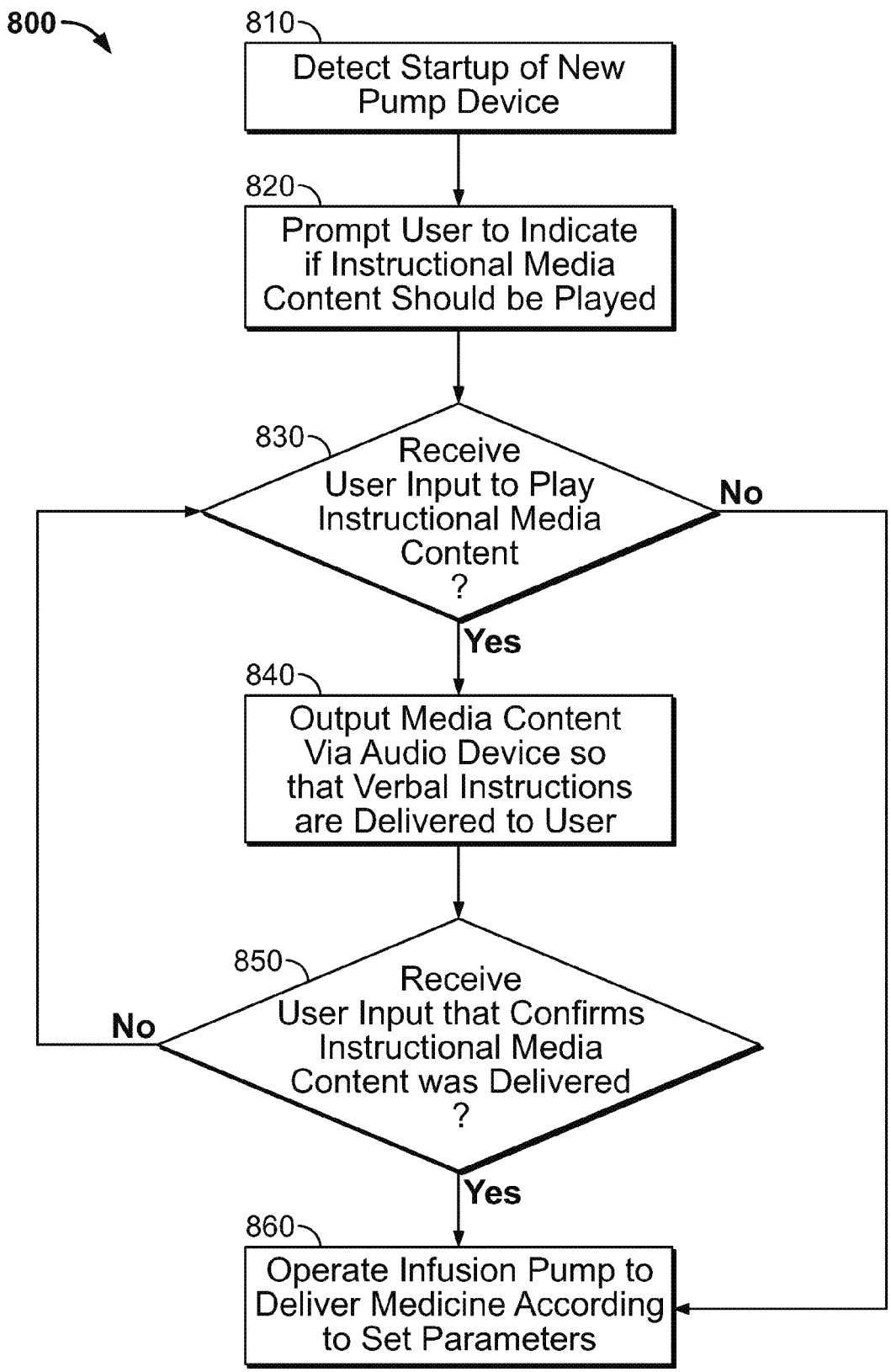
FIG. 26 is a chart describing a process for delivering instructional media content to a user of an infusion pump system, in accordance with some embodiments.

Referring now to FIG. 26, the infusion pump system 10 depicted in FIGS. 1-3 can be configured to provide instruction media content to the user in response to a detected event. As such, the pump system 10 can execute a process 800 that permits a rev user to readily receive a tutorial or other instructions related to the pump system 10. It should be understood from the description herein that the system 400, 500, and 600 can also be configured to operate as described in FIG. 26 so as to provide instruction media content to the user.

The process 800 includes the operation 810 of detecting an event, such as the startup of a new pump device in this particular embodiment. Thereafter, the process 800 proceeds to operation 820 in which the user is prompted to indicate if instructional media content should be delivered to the user. The instruction media content can be related to the detected event. For example, in this embodiment the event is the startup of a new pump device. As such, the instructional media content may comprise an audio tutorial that relates to the preparation of the new pump device in order to begin dispensing medicine to the user, in operation 830, the pump system 10 receives user input that indicates if the instructional media content should be played (e.g., playback through the external audio device 231). If the user indicates "no," the instructional content is not provided and the process 800 proceeds to operation 860 in which the pump system delivers medicine according to set parameters. Alternatively, if the user indicates "yes," the process 800 continues to operation 840 so that the instructional content is output via an audio device (e.g., external audio device 231 having earbuds or the like). In such circumstances, the playback system 23G can provide verbal instructions to the user.

After the instructional content is provided, the process 800 may proceed to operation 850 to query the user on whether the instruction content was properly received. It "no," the process 800 cycles back to operation 830 to determine if the instructional media content should be played to the user. If the user indicates "yes" for operation 850, the process 800 proceeds to operation 860 in which the pump system delivers medicine according to set parameters.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
   a portable, wearable housing defining an interior space to receive insulin;
   a pump drive system positioned in the portable housing and configured to dispense insulin to a user from the portable, wearable housing when the insulin is received in the space; and
   a controller in communication with the pump drive system positioned in the portable, wearable pump housing so as to transmit activation signals for the pump drive system, the controller including a user interface comprising at least a display device and an audio output device, the controller further including a memory device that stores digital music content for playback through the audio output device;
   wherein a pump parameter related to dispensation of the insulin from the portable, wearable housing is adjustable in response to user input at the user interface;
   wherein the controller is configured to output an audible alert through the audio output device, the audible alert being indicative of a detected alarm condition of the infusion pump system, wherein outputting the audible alert includes stopping playback of the digital music content and displaying a message on the display device indicating that playback of the digital music content has been stopped due to the detected alarm condition;
   wherein the controller is further configured to restart playback of the digital music content through the audio output device in response to the controller receiving user input on the user interface indicating that the detected alarm condition is acknowledged or resolved; and
   wherein the controller is further configured to output a different audible alert through the audio output device in response to detection of a different detected alarm condition, the different detected alarm condition being of a different type than the detected alarm condition, wherein outputting the different audible alert includes temporarily stopping playback of the digital music content and automatically resuming playback of the digital music content after outputting of the different audible alert.

2. The system of claim 1, wherein the controller is further configured to output a visual alert through the display device, the visual alert being indicative of the detected alarm condition.

3. The system of claim 1, wherein the controller is further configured to automatically resume playback of the digital music content after outputting of the different audible alert without receiving user input on the user interface indicating that the different detected alarm condition is acknowledged or resolved.

4. The system of claim 1, wherein:
   the detected alarm condition requires immediate intervention; and
   the different detected alarm condition does not require immediate intervention.

5. The system of claim 1, wherein the controller is further configured to determine that the detected alarm condition is resolved and restart playback of the digital music content through the audio output device in response in to determining that the detected alarm condition is resolved.

6. The system of claim 1, wherein the controller is further configured to determine that the detected alarm condition is not resolved and continue outputting the audible alert through the audio output device in response to determining that the detected alarm condition is not resolved.

7. The system of claim 6, wherein the controller is further configured to enter an emergency mode of operation in response to determining that the detected alarm condition is not resolved.

8. The system of claim 7, wherein entering the emergency mode of operation includes outputting a series of incrementally louder alarms.

9. The system of claim 1, wherein the user interface of the controller contemporaneously displays insulin delivery information and media content playback information on a display screen of the user interface.

10. The system of claim 1, wherein the audible alert includes instructions on how to respond to the detected alarm condition.

11. A method of using a medical infusion pump system, comprising:
    outputting digital music content through an audio output device of a medical infusion pump system, the medical infusion pump system comprising:
       a portable, wearable housing defining an interior space to receive insulin;
       a pump drive system positioned in the portable housing and configured to dispense insulin to a user from the portable, wearable housing when the insulin is received in the space; and
       a controller in communication with the pump drive system positioned in the portable, wearable pump housing so as to transmit activation signals for the pump drive system, the controller including a user interface comprising at least a display device and the audio output device, the controller further including a memory device that stores the digital music content for playback through the audio output device;
    detecting, by the controller, an alarm condition of the medical infusion pump system;
    stopping, in response to detecting the alarm condition, playback of the digital music content through the audio output device;
    outputting, in response to detecting the alarm condition and after stopping playback of the digital music content, an audible alert through the audio output device, the audible alert being indicative of the detected alarm condition;
    displaying, on the display device, a message indicating that playback of the digital music content has been stopped due to the detected alarm condition;
    receiving user input on the user interface indicating that the detected alarm condition is acknowledged or resolved;
    restarting playback of the digital music content through the audio output device in response to receiving the user input;
    detecting, by the controller, a different alarm condition of the medical infusion pump system, the different alarm condition being of a different type than the alarm condition;
    temporarily pausing playback of the digital music content through the audio output device in response to detecting the different alarm condition;
    outputting, in response to detecting the alarm condition and after temporarily pausing playback of the digital music content, a different audible alert through the audio output device, the different audible alert being indicative of the different alarm condition; and
    automatically resuming playback of the digital music content after outputting the different audible alert through the audio output device.

12. The method of claim 11, further comprising displaying, on the display device, a visual alert indicative of the detected alarm condition, the visual alert including instructions on how to respond to the detected alarm condition.

13. The method of claim 11, wherein automatically resuming playback of the digital music content after outputting the different audible alert through the audio output device is performed without receiving user input on the user interface indicating that the different detected alarm condition is acknowledged or resolved.

14. The method of claim 11, further comprising:
   determining, by the controller, that the detected alarm condition is resolved; and
   restarting playback of the digital music content through the audio output device in response determining that the detected alarm condition is resolved.

15. The method of claim 11, further comprising:
   determining, by the controller, that the detected alarm condition is not resolved; and
   continuing to output the audible alert through the audio output device in response to determining that the detected alarm condition is not resolved.

16. The method of claim 15, further comprising entering, by the controller, an emergency mode of operation in response to determining that the detected alarm condition is not resolved.

* * * * *